(12) United States Patent
Fahl et al.

(10) Patent No.: US 7,045,550 B2
(45) Date of Patent: May 16, 2006

(54) POLYAMINES AND ANALOGS FOR PROTECTING CELLS DURING CANCER CHEMOTHERAPY AND RADIOTHERAPY

(75) Inventors: William E. Fahl, Madison, WI (US); John Kink, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 122 days.

(21) Appl. No.: 10/214,917

(22) Filed: Aug. 7, 2002

(65) Prior Publication Data

US 2003/0118539 A1    Jun. 26, 2003

Related U.S. Application Data

(60) Provisional application No. 60/342,932, filed on Dec. 20, 2001, provisional application No. 60/337,382, filed on Nov. 5, 2001, provisional application No. 60/317,768, filed on Sep. 6, 2001, provisional application No. 60/310,634, filed on Aug. 7, 2001.

(51) Int. Cl.
  *A61K 31/195* (2006.01)
  *A61K 31/13* (2006.01)

(52) U.S. Cl. ............... 514/565; 514/564; 514/673; 514/674

(58) Field of Classification Search ............ 514/565, 514/564, 673, 674
See application file for complete search history.

(56) References Cited

U.S. PATENT DOCUMENTS

| | | | |
|---|---|---|---|
| 4,720,489 A * | 1/1988 | Shander | 514/171 |
| 4,935,449 A | 6/1990 | Bey et al. | 514/671 |
| 4,996,057 A * | 2/1991 | Schoeff et al. | 514/21 |
| 5,091,576 A | 2/1992 | Bergeron | 564/367 |
| 5,109,024 A | 4/1992 | Prakash et al. | 514/674 |
| 5,137,888 A * | 8/1992 | Bazzano | 514/250 |
| 5,217,964 A | 6/1993 | Edwards et al. | 514/104 |
| 5,354,782 A | 10/1994 | Edwards et al. | 514/655 |
| 5,434,135 A | 7/1995 | Parikh et al. | 514/12 |
| 5,434,145 A | 7/1995 | Edwards et al. | 514/108 |
| 5,648,355 A | 7/1997 | Theoharides | 514/255 |
| 5,654,484 A | 8/1997 | Prakash et al. | 564/511 |
| 5,677,350 A | 10/1997 | Frydman | 514/655 |
| 5,679,682 A | 10/1997 | Bergeron | 514/256 |
| 5,681,837 A | 10/1997 | Bergeron | 514/256 |
| 5,735,263 A | 4/1998 | Rubsamen et al. | 424/450 |
| 5,753,714 A | 5/1998 | Stemerick et al. | 514/654 |
| 5,827,894 A | 10/1998 | Bergeron | 514/674 |
| 5,843,959 A * | 12/1998 | Bergeron, Jr. | 514/316 |
| 5,866,613 A | 2/1999 | Bergeron | 514/674 |
| 5,889,061 A | 3/1999 | Frydman et al. | 514/674 |
| 5,994,339 A | 11/1999 | Crapo et al. | 514/185 |
| 6,030,948 A * | 2/2000 | Mann | 514/12 |
| 6,034,139 A | 3/2000 | Bergeron | 514/654 |
| 6,114,394 A | 9/2000 | Edwards et al. | 514/646 |
| 6,147,262 A | 11/2000 | Bergeron | 564/512 |
| 6,172,261 B1 | 1/2001 | Vermeulin et al. | 564/84 |
| 6,174,261 B1 | 1/2001 | Watanabe et al. | 564/84 |
| 6,239,119 B1 * | 5/2001 | Stogniew et al. | 514/131 |
| 6,573,290 B1 * | 6/2003 | Love | 514/406 |
| 2002/0019338 A1 * | 2/2002 | Hebert | 514/2 |

FOREIGN PATENT DOCUMENTS

| | | |
|---|---|---|
| EP | 0 162 413 A2 | 11/1985 |
| EP | 0 270 349 B1 | 6/1988 |
| EP | 0 277 635 B1 | 8/1988 |
| EP | 0 311 068 B1 | 4/1989 |
| EP | 0 686 142 | 12/1995 |
| EP | 0 884 046 A1 | 12/1998 |
| EP | 1 085 011 A1 | 3/2001 |
| JP | 2000-327537 * | 11/2000 |
| WO | WO 93/18760 | 3/1993 |
| WO | WO 94/07480 | 4/1994 |
| WO | WO 94/19311 | 9/1994 |
| WO | WO 96/23490 | 8/1996 |
| WO | WO 99/51213 | 10/1999 |
| WO | WO 00/05186 | 2/2000 |
| WO | WO 00/16763 | 3/2000 |
| WO | WO 00/46187 | 8/2000 |
| WO | WO 00/66587 | 11/2000 |
| WO | WO 00/78289 | 12/2000 |
| WO | WO 01/14464 | 3/2001 |
| WO | WO 01/72685 A2 | 10/2001 |
| WO | WO 02/38105 A2 | 5/2002 |

OTHER PUBLICATIONS

Aphramaian, M., et al., "Transmucosal passage of polyalkylcyanoacrylate nanocapsules as a new drug carrier in the small intestine," *Biol. Cell*, 1987, 61, 69-76.

Basu, H.S., et al., "The interaction of spermine and petamines with DNA," *Biochem J.*, 1987, 244, 243-246.

Basu, H.S., et al., "Effects of variation in the structure of spermine on the association with DNA and the induction of DNA conformational changes," *Biochem. J.*, 1990, 269, 329-334.

Basu, H.S., et al., "Correlation between the effects of polyamine analogues on DNA conformation and cell growth," *Cancer Res.*, 1989, 49, 5591-5597.

Basu, H.S., et al., "Interaction of a polyamine analogue, 1,19-bis-(Ethylamino)- 5,10,15-triazanonadecane (BE-4-4-4-4), with DNA and effect on growth, survival, and polyamine levels in seven human brain tumor cell lines," *Cancer Res.*, 1993, 53, 3948-3955.

(Continued)

*Primary Examiner*—Kevin E. Weddington
(74) *Attorney, Agent, or Firm*—Woodcock Washburn LLP

(57) ABSTRACT

Polyamine effectors are administered locally to provide protection against the adverse side-effects of chemotherapy or radiation therapy, such as alopecia, mucositis and dermatitis. Pharmaceutical preparations comprising one or more polyamine effectors formulated for topical or local delivery to epithelial or mucosal cells are disclosed. Methods of administering the pharmaceutical preparations are also disclosed.

10 Claims, 2 Drawing Sheets

OTHER PUBLICATIONS

Bergeron, C.J., et al., "Two polyamine analogs (BE-4-4-4 and BE-4-4-4-4) directly affect growth, survival and cell cycle progression in two human brain tumor cell lines," *Cancer Chemother Pharmacol*, 1995, 36, 411-417.

Chen G., et al., "Protection against cyclophosphamide-induced alopecia and inhibition of mammary tumor growth by topical 1,25-dihydroxyvitamin $D_3$ in mice," *Int. J. Cancer*, 1998, 75, 303-309.

Creaven, P.J., et al., "Unusual central nervous system toxicity in a phase I study of $N^1 N^{11}$ diethylnorspermine in patients with advanced malignancy," *Invest. New Drugs*, 1997, 15, 227-234.

Davis, S.T., et al., "Prevention of chemotherapy-induced alopecia in rats by CDK inhibitors," *Science*, Jan. 5, 2001, 291, 134-137.

Desai, M.P., et al., "The mechanism of uptake of biodegradable microparticles in caco-2 cells in size dependent," *Pharm. Res.*, 1997, 14(11), 1568-1573.

Fuerstein, B.G., et al., "Molecular dynamics of spermine—DNA interactions: sequence specificity and DNA bending for a simple ligand," *Nucl. Acids Res.*, 1989, 17(17), 6883-6893.

Hahm, H.A., et al., Phase I study of $N^2 N^{11}$-diethylnorspermine in patients with non-small cell lung cancer, *Clin. Cancer Res.*, Mar. 2002, 8, 684-690.

Hillery, A.M., et al., "Comparative, quantitative study of lymphoid and non-lymphoid uptake of 60nm polystyrene particles," *J. Drug Targeting*, 1994, 2, 151-156.

Ho, D., et al., "Quantitative significance of glutathione and glutathione-S-tranferase in regulating benzo[a]pyrene *anti*-diol-epoxide level in reconstituted C3H/10T1/2 cell iysates, and comparison to rat liver," *Carcinogenesis*, 1984, 5(2), 143-148.

Ho, D., et al., "Modification of glutathione levels in C3H/10T1/2 cells and its relationship to benzo(a)otrebe *anti*-7,8-dihydrodiol 9,10-expoxide-induced cytotoxicity," *J. Biol. Chem.*, 1984, 259(18), 11231-11235.

Hussein, A.M., et al., "Protection from chemotherapy-induced alopecia in a rat model," *Science*, 1990, 249, 1564-1566.

Jimenez, J.J., et al., "Treatment with ImuVert/Nacetylcysteine protects rats from cyclophosphamide/cytarabine-induced alopecia," *Cancer Investigation*, 1992, 10(4), 271-276.

Kramer, D.L.,et al., "Polyamine depletion in human melanoma cells leads to $G_1$ arrest associated with induction of $p21^3$ WAF1/CIP1/SD11, changes in the expression of p21-regulated genes, and a senescence-like phenotype," *Cancer Res.*, 2001, 61, 7754-7762.

Masuda, K., et al., "Response of previously irradiated mouse skin to a second course of irradiation: early skin reaction and skin shrinkage," *Int. J. Radiation Oncl. Biol. Phys.*, 1986, 12, 1645-1651.

Morgan, D.M.L., "Polyamines—an overview," *Molecular Biotechnology*, 1999, 11, 229-250.

Reddy, et al., "*Cis*-Unsaturated analogues of 3,8,13,18,23-pentaazapentacosane (BE-4-4-4-4): synthesis and growth inhibitory effects on human prostate cancer cell lines," *J. med. Chem.*, 2001, 44, 404-417.

Reddy, et al., "Conformationally restricted analogues of $^1N, ^{12}N$-bisethylspemine: synthesis and growth inhibitory effects on human tumor cell lines," *J. Med. Chem.*, 1998, 41, 4723-4732.

Saminathan, M., et al., "Ionic and structural specificity effects of natural and synthetic polyamines on the aggregation and resolubilization of single-, and triple-stranded DNA," *Biochemistry*, 1999, 38, 3821-3830.

Sonis, S.T., et al., "Defining mechanisms of action of interleukin-11 on the progression of radiation-induced of oral mucositis in hamsters," *Oral Oncology*, 2000, 36, 373-381.

Spotheim-Maurizot, M., et al., "Radioprotection of DNA by polyamines," *Int. J. Radiant, Biol.*, 1995, 68(5), 571-577.

Streiff, R.R., et al., "Phase 1 study of $N^1 N^{11}$-diethylnorspermine (DENSPM) administered TID for 6 days in patients with advanced malignancies," *Invest. New Drugs*, 2001, 19, 29-39.

Valasinas, et al., "Conformationally restricted analogues of $^1N, ^{14}N$-bisethylhomospemine (BE-4-4-4): synthesis and growth inhibitory effects on human prostate cancer cells," *J. Med. Chem.*, 2001, 44, 390-403.

U.S. Appl. No. 09/565,714, filed May 5, 2001, Fahl et al.

PCT International Search Report dated Dec. 20, 2002 (PCT/US02/25216).

* cited by examiner

POLYAMINES AND ANALOGS FOR PROTECTING CELLS DURING CANCER CHEMOTHERAPY AND RADIOTHERAPY

This application claims benefit of U.S. Provisional Application No. 60/342,932, filed Dec. 20, 2001, U.S. Provisional Application No. 60/337,382, filed Nov. 5, 2001, U.S. Provisional Application No. 60/317,768, filed Sep. 6, 2001, and U. S. Provisional Application 60/310,634, filed Aug. 7, 2001. The contents of each of these provisional applications are incorporated by reference herein in their entireties.

Pursuant to 35 U.S.C. §202, it is acknowledged that the U.S. Government has certain rights in the invention described herein, which was made in part with funds from the National Institutes of Health, Grant No. CA22484.

FIELD OF THE INVENTION

The present invention relates to the field of cancer therapy. In particular, the invention provides novel compositions and methods for reducing or preventing toxic side effects of radiotherapy and cancer chemotherapeutic agents using polyamine effector molecules locally delivered to cells of the scalp, skin, oral, gastrointestinal and urogenital mucosa.

BACKGROUND OF THE INVENTION

Several patents and printed publications are referenced in this application in order to more fully describe the state of the art to which this invention pertains. The disclosure of each of these publications is incorporated by reference herein, in its entirety.

Presently, surgery, radiation therapy, and chemotherapy are the primary treatment modalities for cancer. Over the past several decades, chemotherapy and radiation therapy coupled with surgery have contributed to a significant reduction in cancer mortality. However, the potential utility of chemotherapeutic drugs and radiation therapy in the treatment of cancer have not been fully exploited due to adverse effects associated with the nonspecific cytotoxicity of these agents or treatments. Alkylating agents used alone or in combination with other chemotherapeutic agents, are used in approximately half of all chemotherapy treatments. Alkylating agents interfere with the proliferation of cancerous cells by inhibiting DNA replication. Non-alkylating cancer chemotherapy drugs are also toxic to mammalian cells; they can inhibit multiple sites within a replicating cell, such as (1) synthesis of nucleotides required for DNA replication and (2) microtubule function required for mitosis, to name just two. Radiation therapy, which achieves most of its cell killing properties by generating oxygen radicals within cells, can also efficiently kill mammalian cells. Cell death is then accomplished by lethal DNA mutations that prevent cell function and division.

The foundation for both radiation and chemotherapy is to target and kill rapidly growing cells. Selective killing of only cancer cells while sparing normal functioning cell populations remains the greatest challenge in cancer therapy. The medical literature describes many major side effects from cancer treatments. All are outcomes of the unwanted killing of normal, non-neoplastic cells. These side effects from chemotherapy and/or radiation therapy range from mild to life-threatening. There is a large effort to increase the selectivity of cancer chemotherapies, but currently, very few such compounds exist. As a result, persons being treated with one or more of these cancer therapies commonly develop numerous clinical complications.

The toxicity of cancer therapy for epithelial cells accounts for many of the side effects commonly suffered by persons undergoing a regimen of chemotherapy or radiotherapy. These include gastrointestinal distress, nausea, vomiting, diarrhea, loss of appetite, hair loss, bone marrow suppression and skin rash or ulceration at the site of irradiation. These complications can be so difficult to endure that it is not uncommon for people to forego or discontinue recommended cancer therapy treatments in order to avoid the side effects. Gastrointestinal disturbances may compromise a patient's chances of recovery, because they make it difficult for the patient to obtain the nourishment necessary to optimize his ability to fight disease. It appears that chemo- and radiotherapy-associated death and sloughing of GI lumenal cells results in a release of GI damage-associated molecules into the vasculature. These blood-borne molecules, when detected by sites within the brain, trigger the nausea response that is so common among patients receiving chemotherapy. Present treatments with drugs, such as Ondansetron, serve to suppress these brain centers and thus diminish the nausea response. However, the primary destruction of the GI lining still limits the most effective use of chemotherapy. A better mechanism to diminish nausea in these patients would be to eliminate the primary destruction of the GI surface and thus prevent the release of damage-associated, nausea-inducing molecules, rather than just suppressing the effects of these molecules in the brain. Typically, during the course of chemotherapy, the chemotherapeutic agent is administered in sub-optimal doses in order to minimize toxicity and to protect normal, drug-sensitive cells. Reducing the sensitivity of normal cells to chemotherapeutic agents would allow the administration of higher drug dosages and chemotherapy could be rendered more effective.

An especially insidious side effect from chemotherapy and/or radiation therapy is alopecia. Alopecia or hair loss is the most common hair growth disorder in humans and is often the cause of great concern in affected individuals. In patients with acquired alopecia associated with cancer chemotherapy or radiation therapy, the loss of hair ranked above vomiting as an important concern. A National Cancer Institute (NCI) study has indicated that hair loss during chemotherapy is the most psychologically debilitating aspect of cancer treatment. It is estimated that approximately 60–70% of all patients receiving cancer chemotherapy experience alopecia. Hair loss represents a psychologically distressing effect that can cause negative changes in body image, decreased social activity and altered interpersonal relationships and may lead to refusal of further chemotherapy.

The phenomenon of chemotherapy-induced alopecia is believed to result from cytotoxic and apoptosis-related damage to the hair follicle. The pathobiologic mechanisms that underlie chemotherapy induced follicle damage are characterized by bulging of the dermal papilla, kinking and distension of the follicular canal and disruption of the melanogenic apparatus.

Several approaches have been employed in an attempt to protect patients from chemotherapy-induced alopecia. These have included physical modules that temporarily decrease scalp blood flow and drug contact time with the hair follicle, but the patient tolerance was very poor. These poor results led to the development of scalp cooling methods that decrease both the metabolic rate of follicular stem cells and blood flow to the follicle matrix, but this strategy was found to be unsuccessful. The use of dietary alpha-tocopherol, a free radical scavenger, was shown to have a protective effect in rabbits but not in humans. Minoxidil 2% solution was also found to be ineffective in treating chemotherapy-induced alopecia. Pre-treatment of rodents with growth factors and cytokines provided some degree of protection against alopecia induced by ARA-C (cytosine arabinoside) but not the commonly used cancer drug cytoxan.

Reversal of cyclophosphamide-or cyclophosphamide/cytarabine-induced alopecia by N-acetylcysteine (NAC) or NAC/ImmuVert, administered parenterally or applied topically in liposomes, has been reported in a rat model system (Jimenez et al., Cancer Investigation 10: 271–276, 1992). NAC is a precursor of glutathione and, as such, is believed to function as a detoxifying agent by increasing intracellular GSH levels. This sort of therapy is limited in efficacy, inasmuch as it has been shown that intracellular GSH levels can only roughly double in a cell by adding exogenous NAC. (See Ho & Fahl, 1984, J. Biol. Chem. 259: 11231–11235; Carcinogenesis 5: 143–148, 1984).

Compounds that can preferentially slow the growth of normal cells susceptible to cancer therapy are alternative strategies to prevent chemotherapy-induced alopecia. Antiproliferative agents such as vitamin D derivatives, or cell-cycle inhibitors such as small molecule CDK-2 inhibitors that inactivate certain proteins involved in cell cycle progression have been tested. Unfortunately, most have met with mixed results. Reports indicate that many of these compounds have performed poorly or were irreproducible in preclinical animal studies, or have failed outright in clinical trials.

U.S. Pat. No. 5,753,263 to Lishko et al. discloses methods and compositions for treating alopecia induced by certain chemotherapeutic agents, which comprise topical application of an effective amount of a p-glycoprotein, or MDR gene encoding such a protein, in a liposome carrier. Successful delivery of these proteins and genes to target cells was not demonstrated. Moreover, even if shown to be effective, this therapy is limited to the particular chemotherapeutic agents that can be exported from a cell via the p-glycoprotein pump. Notably excluded from this list are alkylating chemotherapeutic agents.

Thus, while treatments of the types outlined above may provide some relief from chemotherapy-induced hair loss, their utility is limited. Therefore, there remains a continued search for effective compounds that can safely prevent chemotherapy or radiation-induced alopecia.

Radiation-induced dermatitis is another major side effect of cancer treatment. Radiotherapy used regularly as a primary or adjunct therapy, remains largely a nonspecific treatment approach. However, radiotherapy can equally and indiscriminately kill normal dermal cells as well as underlying cancer cells.

Of the many thousand women in the US who will be diagnosed with breast cancer in 1999, a large percentage will receive radiation therapy. It is estimated that 87% of these women will develop some degree of radiation-induced dermatitis, varying from mild to brisk erythema, moist desquamation or even permanent scarring. It is estimated that the severe forms of dermatitis occur in about 60% of all patients receiving palliative radiotherapy. Radiation-induced dermatitis can impose significant and painful discomfort and interfere with the quality of life. It can lead to serious irritation, bacterial infections and in the worst scenario it can cause the suspension of critical cancer treatment. While there has been much attention to how radiation affects the skin, very little research has been performed on identifying and standardizing clinical intervention. A survey of Radiation Therapy Oncology Group (RTOG) institutions in 1995, revealed that 50% of the RTOG institutions used Aloe Vera gel as the treatment of choice. Unfortunately, a study completed in 1991 by the North Central Cancer Treatment Group (NCCTG), reported that Aloe Vera gel did not protect against radiation-induced dermatitis when used prophylatically in women undergoing breast cancer therapy. Alternative compounds used in the survey included Aquaphor (Biersdorf, Lindenhurst, N.Y.), Carasyn Gel or lanolin.

Some of the newer compounds developed to treat radiation-induced dermatitis function either as better moisturizers or are designed to prevent inflammation in the skin. Moisturizers currently being tested, either singly or in combination are Acemannan, a wound dressing gel, Biafine, and Lipiderm. A recent randomized trial indicated that neither Biafine nor Lipiderm seem to have a radio-protective effect. Mixed results have been seen using anti-inflammatory compounds such as a topical cortisone or corticosterioid (mometasone furoate) cream. Interferon gamma treatments have been shown to reduce a severe form of radiation dermatitis, cutaneous radiation fibrosis. Unfortunately, most of these classes of compounds were found to be not very effective when tested in clinical trials.

Sulfhydryl containing aminothiol compounds have shown some promise as therapies to protect against radiation induced-mutations and carcinogenesis. DNA damage by radiation is due largely to the action of free radicals. It is thought that these aminothiol-radioprotectors can serve as free-radical scavengers to reduce this critical damage. In 1959, the U.S. Army initiated an Antiradiation Drug Development Program in which over 4000 compounds were synthesized and tested for their radio-protective abilities. The best radio-protectors contained cysteine, and one compound, S-2-(3-aminopropylamino) ethylphosphorothioic acid, also called WR-2721 or amifostine, provided the best protection thus far. Several studies have shown that this compound administered systemically shows a protective effect against the side effects of radiotherapy. U.S. Pat. Nos. 5,217,964, 5,354,782, 5,434,135 and 6,114,394 also disclose polyamine derivatives asserted to have a radioprotective effect when systemically administered to a subject. The need for systemic administration of these compounds is a significant disadvantage, inasmuch as they could consequently exert a protective effect on the tumor cells themselves, or otherwise have a detrimental effect on non-target organs and tissues, as has been observed in certain clinical trials of systemically administered polyamines that were halted because of very significant host organ toxicity, including severe constipation and neurological toxicity. Adverse reactions, including gastrointestinal and neurological toxicity, during systemic, e.g., intravenous regimens of DENSPM (BE333) also have been noted (Creaven et al. 1997, Invest. New Drugs 15: 227–234; Streiff et al. 2001, Invest. New Drugs 19: 29–39, 2001; Hahm et al. 2002, Clin. Cancer Res. 8: 684–690).

Mucositis is an important and costly side effect of cancer therapy. Mucositis, or inflammation of the mucosal lining, is frequent and a potentially severe complication from chemotherapy and/or radiotherapy. It can manifest as erythema, desquamation, ulcer formation, bleeding and exudate. It is generally accepted that mucositis results from the direct inhibitory effects of chemotherapy or radiotherapy on DNA replication and mucosal cell proliferation. These events result in the reduction in the regeneration capability of the basal epithelium leading to mucosal atrophy, collagen breakdown and ulceration. A secondary effect is infection from a number of pathogens after the breakdown of the protective mucosal barrier.

Mucositis can be present anywhere throughout the gastrointestinal and urogenital tract, from the oral cavity to the intestines and rectum. It is particularly debilitating because it can lead to abnormal nutrition, increased systemic infections, use of narcotics to diminish pain, and postponement of cancer therapy. Patient-related risk factors for mucositis include, hematological malignancies and poor oral health. Therapy-related risk factors include, the chemotherapy used (e.g., antimetabolites), dose of drug or radiation, and concomitant therapy. Oral mucositis is a complication in 40% of patients receiving chemotherapy, and in 75% of those exposed to high dose chemotherapy with bone marrow transplantation. The prevalence of gastrointestinal mucositis has been reported to range from 30–39%, although prevalence from 40% to 75% has been reported for antimetabolites such as 5-fluorouracil. In addition, more than 90% of patients irradiated for head and neck cancer experience oral mucositis. Consequently, complications relating to mucositis from chemotherapy and/or radiotherapy lead to increased morbidity, the need for parenteral nutrition, and increased costs of hospitalization.

Presently, no commercial drugs are believed to be available specifically designed to prevent mucositis due to cancer therapy. Only simple preventative measures now exist for oral mucositis involving basic principles of oral hygiene and therapies such as topical anesthetics and systemic analgesics to relieve pain. Auxiliary preventative measures to protect normal cells of the GI tract involve nutrient stimulation and maximizing the intake of growth factors. However, those therapies are primarily superficial approaches which do not address the cause of mucositis. Therefore, there is a real need for safe and effective drugs that can effectively reduce mucositis from cancer therapy.

Approaches into the prevention of mucositis induced by cancer therapy can be divided into three broad categories: One approach promotes mucosal alterations using mucosally active modifiers to reduce delivery and secretion of the chemotherapeutic agent to mucosal cells; the second focuses to increase or modify the proliferative capabilities of the mucosa, and the third aims to reduce the potential for infections and inflammation. The value of using delivery and secretion modifiers such as propantheline or pilocarpine, that can either decrease or increase salivation, respectively, is presently being evaluated. Investigators have studied various agents that modify epithelial proliferation. These include certain cytokines, (granulocyte colony-stimulating factor, (G-CSF); granulocyte-macrophage colony-stimulating factor, (GM-CSF)), beta-carotene, and glutamine. However, these compounds have either failed to show benefits in placebo-controlled clinical trials (e.g., glutamine) or the clinical data is lacking (e.g., G-CSF, GM-CSF). Studies using the anti-microbial/anti-inflammatory approach have shown some benefit in oral mucositis after radiation. Lozenges containing polymyxin B, tobramycin, and amphotericin B prevented oral infections. This approach, while a useful supplementary therapy, fails to treat the direct causes of mucositis. Overall, while some agents have been identified that may be able to accelerate healing and alter the progression of mucositis, currently no intervention exists that is successful at preventing mucositis.

It is clear from the foregoing discussion that there exists a significant unmet medical need to identify novel agents that can prevent and/or treat the side effects of cancer therapies. The successful implementation of protective therapies that promote routine growth and proliferation of normal cells in the presence of radiotherapy or chemotherapeutic agents will permit the use of higher dose, more aggressive chemotherapy. Consequently, these protective therapies may not only address the side effects of cancer but may enable greater efficacy against cancer than that seen using current therapies. Two important targets for development of such protective therapies are (1) the epithelial cells lining the oral and entire gastrointestinal (GI) or urogenital tract, and (2) the epithelial cells of the skin, including hair follicles and the epidermis. While certain treatments of the types outlined above may provide some relief from chemotherapy or radiotherapy-induced side effects, their effectiveness and utility is limited, underscoring the requirement for new effective therapies.

SUMMARY OF THE INVENTION

In accordance with the present invention, a novel and effective strategy has been devised for protecting rapidly dividing normal cells from damage during the course of radiotherapy or chemotherapy to treat a cancer, or in connection with other conditions for which chemotherapy or radiation therapy are employed, e.g., bone marrow transplant. This strategy is based on the use of polyamines, polyamine analogs, and inhibitors of polyamine biosynthesis and metabolism to prevent and treat the adverse side effects of cancer therapies. This class of compounds is termed herein as polyamine effectors. Through one or more of several mechanisms, these polyamine effectors function to reduce the sensitivity of normal, non-neoplastic cells to the harmful effects of conventional cancer chemotherapies and radiotherapy.

Specifically, this invention relates to topical delivery of polyamine effectors to locally protect the normal epithelial cells in the skin, hair follicles, and mucous membranes of the gastrointestinal and urogenital tract of cancer patients during cancer chemotherapy or radiotherapy.

According to one aspect of the invention, a composition for protecting non-neoplastic cells from damage during cancer chemotherapy or radiotherapy is provided. The composition comprises one or more polyamine effector agents, as defined below, and a delivery vehicle for locally delivering the agents to a target population of the non-neoplastic cells. In one preferred embodiment, the target cell population comprises epithelial cells lining hair follicles or in the epidermal and dermal layers of skin. In another preferred embodiment, the target cell population comprises epithelial cells of the oral, gastrointestinal, and urogenital mucosa.

A wide variety of compounds have shown efficacy as polyamine effectors, in accordance with the present invention. These include naturally-occurring polyamines and polyamine analogs, particularly (1) analogs comprising functional groups not present on naturally-occurring polyamines (2) long-chain polyamine analogs, and (3) polyamine analogs containing conformational restrictions, as well as modulators of polyamine biosynthesis, degradation and cellular transport. Generally speaking, compounds that are suitable for use exert either an anti-proliferative effect on cells, and/or they function as cellular (specifically DNA) protective agents. Within these broad classes, embodiments of the invention utilize polyamine effectors that (1) modulate activity of a polyamine biosynthetic, catabolic or transport system, (2) protect cells and cellular DNA from damage by reactive oxygen species or free radicals, (3) associates with cellular DNA and displace cellular polyamines and/or alter the cellular DNA structure, which can serve to protect the DNA molecule from radiation and certain chemotherapeutic agents, as well as cause cell cycle arrest. The polyamine effector-containing pharmaceutical preparations of the invention may also comprise at least one other agent that reduces or prevents hair loss, dermatitis, mucositis or gastrointestinal distress caused by treatment with a chemotherapeutic agent or radiation therapy. These include other anti-proliferative agents, as well as chemoprotective inducing agents or free radical scavengers.

The pharmaceutical preparations are formulated in a topical delivery vehicle that, in various embodiments, comprises one or more of liposomes, lipid droplet emulsions, oils, aqueous emulsions of polyoxyethylene ethers, aqueous alcohol mixtures, aqueous ethanol mixtures containing propylene glycol, aqueous ethanol mixtures containing phosphatidyl choline, lysophosphatidyl choline and triglycerides, xanthan gum in aqueous buffer, hydroxypropymethylcellulose in aqueous buffer or aqueous alcohol mixtures, diethylene glycol monoethyl ether in aqueous buffer, and biodegradable microparticles. In formulations for topical delivery to scalp or hair follicles, the delivery vehicle preferably comprises one or more of an aqueous alcohol mixture and propylene glycol. For topical delivery to the skin, the pharmaceutical preparation preferably is formulated as a cream, lotion, ointment or gel.

In formulations for topical delivery to the oral cavity or naso-esophageal passages, the delivery vehicle preferably comprises a mucoadhesive substance, and may be formulated as an aerosol, oral rinse, ointment or gel. For vaginal or rectal delivery, delivery vehicle may also comprise a mucoadhesive substance, and is formulated as a cream, ointment, lotion, gel, foam or suppository.

In embodiments comprising topical delivery to the gastrointestinal tract, the delivery vehicle preferably comprises one or more of nonionic liposomes and mucoadhesive substances, and is typically formulated as a liquid for coating the surface of the gastrointestinal tract.

According to another aspect of the invention, a method is provided for protecting normal (i.e., non-neoplastic) epithelial cells from damage during cancer chemotherapy or radiotherapy. The method comprises administering to a population of epithelial cells the pharmaceutical preparations as described above, for a time and in an amount effective to protect the non-neoplastic cells from damage during the cancer chemotherapy or radiotherapy. In a preferred embodiment, the method is used to prevent alopecia during cancer therapy, by topically applying the composition to the scalp. In another preferred embodiment, the method is used to prevent gastrointestinal distress due to cancer therapy by administering the composition orally. In another preferred embodiment, the method is used to prevent mucositis from chemotherapy or radiotherapy by administering the composition topically to the appropriate region of the body. In yet another preferred embodiment, the method is used to prevent radiation-induced dermatitis, skin rash, and ulceration at the site of irradiation by applying the preparation to the skin.

According to another aspect of the invention, a method of treating cancer in a patient is provided. The method comprises a combination therapy, wherein the patient is administered the chemotherapy or radiation therapy and is also administered one or more of the polyamine effector-containing pharmaceutical preparations described above, where the administration of the polyamine effector reduces or eliminates the toxic side-effects of the cancer therapy and allows administration of higher doses of the chemotherapy or radiotherapy than would be tolerated by the patient without the co-treatment with the polyamine effector.

In preferred embodiments of the foregoing aspects of the invention, the chemotherapeutic agent is one or a combination of different classes of agents such as alkylating agents, antimetabolite inhibitors of DNA synthesis, antitumor antibiotics, mitotic spindle poisons, vinca alkaloids, and topisomerase inhibitors. Specific chemotherapeutic agents include, but are not limited to, altretamine, asparaginase, bleomycin, busulfan, carboplatin, cisplatin, carmustine, chlorambucil, cladribine, cyclophosphamide (cytoxan), cytarabine, dacarbazine, dactinomycin, daunorubicin, doxorubicin, etoposide, floxuridine, fludarabine phosphate, fluorouracil, hydroxyurea, idarubicin, ifosfamide, lomustine, mechlorethamine, nitrogen mustard, melphalan, mercaptopurine, methotrexate, mitomycin, mitoxantrone, paclitaxel, pentostatin, pliamycin, procarbazine, streptozocin, teniposide, thioguanine, thiotepa, vinblastine and vincristine. The radiation therapy consists of all useful types of radiation used in cancer treatment. This includes x-rays, gamma- rays, electron beams, photons, alpha-particles and neutrons.

Various features and advantages of the present invention will be understood from the detailed description and examples that follow.

DETAILED DESCRIPTION OF THE INVENTION

Figure 1:
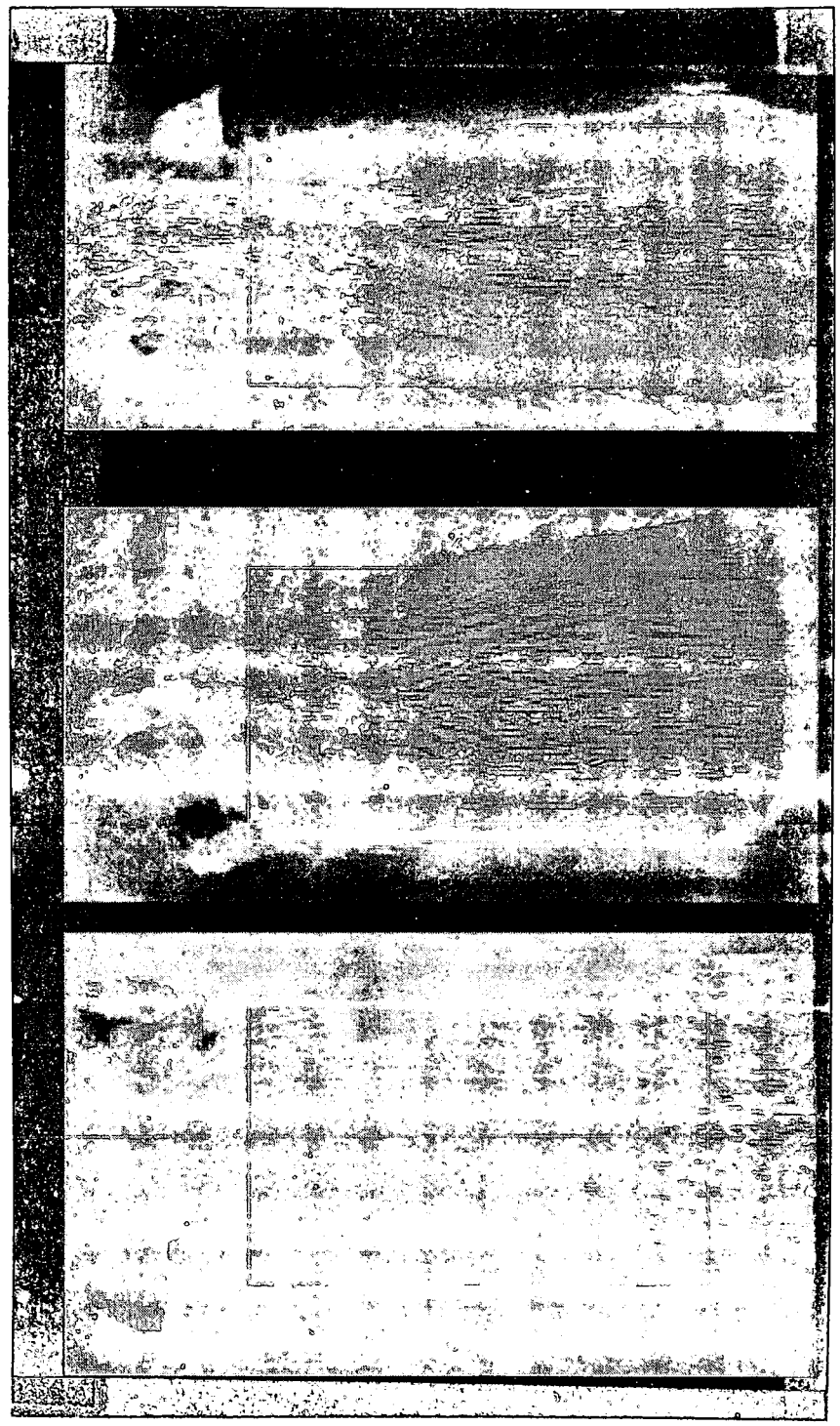
FIG. 1. Effect of polyamines on hair loss in rat pups treated with cytoxan. A topical formulation containing either 10 mM agmatine, 50 mM putrescine or vehicle alone was applied topically, once per day for 10 days to the backs of the animals. Animals received a single injection of cytoxan on day 5 of the topical polyamine treatment. Left panel=vehicle only; center panel=10 mM agmatine; right panel=50 mM putrescine.

The present invention provides compositions and methods for protecting non-cancerous, rapidly dividing cells in a patient's body from the toxic effects of chemotherapeutic agents or radiotherapy administered to the patient. In particular, the compositions and methods of the invention are designed for protecting epithelial cells. Most particularly, the targets are epithelial cells lining hair follicles, epithelial and/or mucosal cells of the skin, mouth, gastrointestinal (GI) and urogenital tract.

Polyamine effectors formulated in delivery vehicles are specifically designed to be administered topically to the skin or surfaces of the mouth, GI or urogenital tract. These mixtures can protect normal, non-neoplastic cells from damage from cancer therapy. By producing a local gradient effect within the tissues, the topically applied polyamine effector produces a local protective effect at the intended region. Importantly, while this local effect protects normal cells, the deeper-seated tumors remain substantially unaffected by the topical polyamine effector and therefore remain sensitive to the cancer therapeutic. Moreover, topical delivery avoids the systemic exposure and concomitant toxicity to major organs and tissues that has been previously observed when polyamine analogs were administered systemically. Protection of normal tissue is accomplished by formulating one or more polyamine effectors in combination with an appropriate delivery vehicle, depending on the administration site (e.g. dermal/intradermal or mucosal). Thus, the polyamine effector-containing compositions of the invention may be applied to any normal cell type susceptible to the side effects of cancer therapy that is accessible by topical delivery.

It has been discovered in accordance with the present invention that polyamine effector compounds can be efficiently delivered to the aforementioned target cell populations, where they are capable of entering the cells and effectively protecting them from the harmful side effects of chemotherapy or radiotherapy. The resultant benefit is the prevention, reduction in severity or alleviation of symptoms associated with chemotherapy or radiotherapy, most notably, hair loss, dermatitis, mucositis and gastrointestinal distress.

A. Polyamine effectors:

The following definitions relating to polyamine effectors will be useful for understanding aspects of the invention.

Polyamine effector. A "polyamine effector" is defined as a class of compound consisting of polyamines, polyamine analogs, and modulators of the polyamine biosynthetic and/or cellular transport pathway, which, when applied locally to non-neoplastic epithelial cells (e.g., hair follicular, dermal, epidermal, gastrointestinal, mucosal), protect those cells from the damaging side-effects of chemotherapy or radiation therapy, such as alopecia, dermatitis, mucositis and gastrointestinal distress.

Polyamine. Polyamines are small aliphatic amines found in all living cells. By nature, polyamines are polycationic. They are biosynthesized from amino acids, such as arginine and ornithine. Examples of common polyamines found in plant and animal cells are: putrescine ($NH_2(CH_2)_3NH_2$), formed by the decarboxylation of ornithine or arginine; spermidine ($NH_2(CH_2)_3NH(CH_2)_4NH_2$); and spermine ($NH_2(CH_2)_3NH(CH_2)_4NH(CH2)_3NH_2$); the latter two being formed by subsequent addition of an aminopropyl moiety to putrescine and spermidine, respectively. Because such polyamines are found in nature, they are sometimes referred to herein as "naturally-occurring" polyamines. However, they may be prepared by a variety of synthetic strategies, as would be known in the chemical arts.

Polyamine analog. The term "polyamine analogs" as used herein refers to polycationic molecules that are similar, but not identical to polyamines found in nature. Polyamine analogs may be branched or unbranched, or may have other structural variations as compared to naturally-occurring polyamines, while retaining the core features of polyamines (multiple amine groups, polycationic). For purposes of the present invention, polyamine analogs are further categorized into three groups: (1) simple polyamine analogs, (2) constrained or conformationally restricted polyamine analogs, and (3) linked or long-chain polyamine analogs.

By "simple polyamine analogs," it is meant that the analog retains the flexibility conferred by the aliphatic carbon backbone, as well as the approximate carbon chain length of naturally-occurring polyamines, but possess a modification or contain one or more added functional groups (e.g., sulfhydryl, phenyl, alkyl) that confers a desired feature or advantage to the molecule.

By comparison, "conformationally restricted polyamine analogs" (sometimes referred to herein as "constrained polyamine analogs" are modified in their carbon backbone to remove flexibility in the modified area, such that two or more amino functionalities in the molecule are restricted to a particular spatial location. Such modification often is accomplished by introducing a cyclic or unsaturated moiety at one or more locations in the carbon backbone, such as is described, for example, in U.S. Pat. No. 5,889,061 and by Valasinas et al. (2001), J. Med. Chem. 44: 390–403.

"Linked or long-chain polyamine analogs" are polyamines that are longer than naturally-occurring polyamines such as spermine. Increasing the overall length of a polyamine may be accomplished, for example, by linking together oligoamines or by adding oligoamine "units" (such as aminopropyl or aminobutyl groups) to a foundation molecule, such as spermine. Thus, while spermine has a 3-4-3 carbon backbone (4 carbons between the two internal amino groups and 3 carbons between each internal amino group and the respective terminal amino groups), linked or long-chain analogs might comprise an additional one, two, three, four or more aminopropyl or aminobutyl groups, for example, on either or both ends of the molecule, and further may comprise terminal methyl or ethyl groups on either or both ends.

It will be appreciated by those of skill in the art that a polyamine analog may possess features of more than one of each of the subcategories defined above. For example, a long-chain polyamine may also comprise a conformational restriction at one or more locations.

Biosynthetic pathway or cellular transport modulator. The term "polyamine biosynthetic pathway or cellular transport modulator" as used herein refers to a compound that (1) inhibits the biosynthesis of polyamines within cells, or accelerates their degradation, the latter which may be accomplished by reversing the polyamine biosynthetic pathway; or (2) inhibits the import, or accelerates the export of polyamines into and out of cells. A biosynthetic pathway or cellular transport modulator typically is a polyamine or a polyamine analog, but need not be.

Antiproliferative. As used herein, the term "antiproliferative" refers to an agent that slows or stops cell division. The antiproliferative agent may exert its effect by reducing the amount of naturally occurring polyamines within a cell, or within the local environment of cellular DNA. It has long been know that reduction of endogenous cellular polyamines has an anti-proliferative effect. The antiproliferative agent alternatively may exert its effect by inhibiting cell cycle progression at one or more stages. Such an agent may be referred to herein as a "cell cycle progression inhibitor." Certain polyamine effectors described herein act as antiproliferatives, specifically cell cycle progression inhibitors, by associating with and modifying the conformation or structure of DNA. These agents are sometimes referred to herein as "DNA modifiers."

Cellular (or DNA) protector: The term "cellular protector" or "DNA protector" refers to agents that protect the cell's enzymes, DNA or other components from the detrimental effect of radiation, free radicals, reactive oxygen species or other molecules of a similar nature, which may be generated through the activity of a chemotherapeutic agent or radiation therapy.

Polyamines are ubiquitous in prokaryotic and eukaryotic cells, where they serve many functions, including modulating the activities of proteins, RNA, DNA, and lipids. Cellular polyamines are thought to be important for normal cell growth and proliferation due to their function in regulating transcriptional and translational stages of protein synthesis. They can also affect chromatin structure in cells by binding specifically to DNA. Thus, they are thought to act with nucleic acids to stabilize and facilitate DNA replication. Polyamine analogs have been studied extensively in relation to cancer research. Indeed, studies have indicated that certain polyamine analogs or inhibitors of the polyamine biosynthetic pathway have potent anti-proliferative effects. With the understanding that the basis of selectivity of current cancer therapy is to target rapidly proliferating cells, the present invention utilizes the characteristic activities of these compounds to reduce the sensitivity of normal, non-neoplastic cells to the harmful effects of conventional cancer chemotherapies and radiotherapy.

Compositions comprising the polyamine effectors described herein are useful against the side effects of cancer therapy by acting at a number of different levels. One way these compounds can protect non-neoplastic cells is by acting as inhibitors of the polyamine biosynthetic pathway or as activators of the polyamine catabolic pathway. It has long been known that reducing the amount of endogenous polyamines in tumor cells confers a strong anti-proliferative effect.

The key enzymes that make up the polyamine biosynthetic/catabolic pathway in mammalian cells are: arginase which converts arginine to ornithine, ornithine decarboxylase (ODC) that forms putrescine from ornithine; S-adenosylmethionine decarboxylase (AdoMetDC) that forms S-adenosylmethionine (dcAdoMet); spermidine synthase that transfers the aminopropyl group from dcAdoMet to putrescine; and spermine synthase that transfers the aminopropyl group from dcAdoMet to spermidine to form spermine. Spermine/spermidine acetyltransferase (SSAT) is an important enzyme involved in polyamine degradation; it retro-converts spermine back to putrescine by acetylation. SSAT, in conjugation with polyamine oxidase (PAO), allows for reversal of the biosynthetic pathway and attenuation of the levels of individual polyamines. Another key regulatory molecule, antizyme, is a critical protein in the maintenance of polyamine homeostasis. It is rapidly produced in response to elevations in cellular polyamine levels and serves to down regulate polyamine synthesis by degrading ODC.

Polyamine effectors that inhibit polyamine biosynthetic enzymes or activate enzymes involved in catabolism of polyamines are suitable for use in the present invention, as are polyamine effectors that can activate an antizyme that in turn degrades ODC and reduces polyamine synthesis. Notably, naturally-occurring polyamines have been shown to be effective biosynthetic pathway inhibitors because they induce a feedback inhibition within cells.

Effectors that can reduce polyamine uptake by inhibiting the cellular polyamine transporter system (PTS) are also suitable for use in the present invention. This approach may be particularly effective when used in combination with any of the other above approaches. Analogs that bind and inhibit the PTS are also suitable, as are small molecule enzyme inhibitors such as difluoromethylornithine hydrochloride (DFMO) that can inactivate ODC in combination with a PTS inhibitor. By selectively slowing the growth rate of rapidly proliferating normal cells, these types of polyamine effectors (or combinations thereof) are particularly useful against the side effects of radiotherapy or chemotherapy.

A different mechanism by which polyamine effectors are useful against the side effects of cancer therapy is by acting directly as a type of protector molecule. Instead of acting on enzymes of the polyamine pathway or the PTS, the effector acts directly as the protective agent. Without intending to be limited to any particular mechanism of action, one way in which certain polyamine analogs may act directly as protective agents is as potent free radical scavengers. Free radical formation after radiation exposure is the primary mechanism of cytotoxicity of radiotherapy. These generated free radicals interact with DNA causing damage that can result in apoptosis and cell death. Reducing the cellular levels of free radicals by polyamine pretreatment of normal cells therefore will protect those cells against DNA-acting cancer therapies. One example of a polyamine analog comprising a free radical scavenging functional group is the thiol analog, amifostine. In the radiation-induced dermatitis assay developed for the present invention, this molecule has demonstrated good radioprotective activity, as compared with putrescine, which is a structurally similar polyamine, but does not contain the nucleophilic sulfhydryl group.

Additionally, by virtue of their extended length, long-chain polyamine analogs are capable of competing with and displacing natural polyamines from their normal binding sites on nucleic acids, particularly DNA, in mammalian cells. At physiologic pH, the amine groups are protonated to each yield a single positive charge, such that as the length of the polyamine increases, the number of positive-charged sites available for hydrogen bonding with DNA increases. As a result, these polyamine analogs have been shown to compete more effectively in vitro (e.g., versus spermine) for binding to DNA, and are also shown to confer conformational changes, such as conversion of B to A and B to Z forms in DNA as well as condensation and aggregation of DNA and chromatin within mammalian cells in vivo (Fuerstein et al., 1989, Nucl. Acids Res. 17: 6883, Basu & Marton 1987, Biochem. J. 244: 243; Basu et al.1989, Cancer Res. 49: 5591; Basu et al. 1990, Biochem. J. 269: 329; Saminathan et al. 1999, Biochemistry 38: 3821). For many electrophilic, alkylating drugs, reaction with DNA occurs in two steps, the first step requiring intercalation between nucleoside bases in helical B DNA, and a rapid second step involving alkyaltion of the adjacent base. By condensing and altering the form of DNA, polyamine analogs can protect cellular DNA from alkylation by electrophilic drugs. Likewise, condensation of DNA by polyamine binding has also been shown in vitro to dramatically reduce the number of single strand breaks induced when the DNA is irradiated (Spotheim, M. 1995, Int. J. Radiat. Biol. 68: 571–577).

Polyamine analogs that have been synthesized to increase the number of —[NH—$(CH_2)_n$] segments in the molecule (e.g., BE-4-4-4 versus BE-4-4-4-4) illustrate the point that as little as one additional —NH—$(CH_2)_n$— segment can enhance DNA binding and the associated ability to cause aggregation of the DNA. BE-4-4-4 binds to DNA in vitro but does not aggregate it, but BE-4-4-4-4 both binds DNA and aggregates it (Basu et al. 1993, Cancer Res. 53: 3948). As set forth in the examples that follow, results from both alopecia and dermatitis studies show that long-chain polyamine analogs are particularly effective in protecting animals against chemotherapy and radiotherapy. These long-chain compounds, such as representative examples SL-11158, SL-11159 and SL-11160 (described in WO 02/38105), represent polyamines in which linking together of single unit polyamines was accomplished to yield molecules with molecular weights of three to five times that of natural polyamines or simple polyamine analogs. Though all of the above polyamine analogs act to deplete mammalian cells of natural polyamines, those that bind DNA and alter its conformation are generally more effective in conferring growth regulation and protection in the alopecia and dermatitis models established in accordance with the invention.

In the experimental examples that follow, the inventors have also demonstrated polyamine analogs, such as SL-11093 and SL-11094 (described in Valasinas et al., 2001, supra and in WO 02/38105), which have been synthesized to contain conformational restriction, to be effective in preventing chemotherapy-induced alopecia. It is believed that by making the structure of the polyamine analog rigid, it will also introduce rigidity and less flexibility into the cellular DNA to which it still binds, and by so doing, serve to diminish the flexible, helical nature of DNA.

The ability of long-chain and conformationally restricted polyamine analogs to alter the flexibility and form of cellular DNA, which may include short regions or 'bubbles' of single-stranded DNA at the site of polyamine binding (Feuerstein et al., 1989, supra), underlies another mechanism by which these analogs act as anti-proliferative agents. Cells possess a complex p53-dependent, sensory and signal transduction system that is constantly scanning and sensing such changes in the form of DNA. For instance, it has been shown that conformational changes in cellular DNA activate a p53-mediated p21 induction pathway that leads to a $G_1$ cell cycle arrest. Investigators in the field (Kramer et al. 2001, Cancer Res. 61: 7754) have demonstrated that polyamine analogs trigger this pathway. To establish that this polyamine-induced, growth regulatory effect is achieved in human skin cells, the inventors treated A431 human epidermoid cells with a one hour daily pulse of polyamine analog for five days. Comparing polyamine-pulsed cells with control cells, the inventors observed a quadrupling in cell number in the control cells, but little or no increase in cell number in the polyamine treated cells. Flow cytometry analysis of DNA content of these cells during the cell cycle showed that the polyamine treated cells had arrested in the $G_1$ phase. The fact that five, daily, one-hour pulses of polyamine to skin cells could induce a $G_1$ cell cycle block provides a useful corroboration to the inventors' application schedule for animal experiments where five, daily topical polyamine analog applications prior to chemotherapy administration have been found, empirically, to yield the best protective effect against alopecia.

To summarize the foregoing discussion, polyamine effectors of the invention may comprise naturally occurring polyamines, simple polyamine analogs containing functional groups that confer a cellular protective effect, long-chain polyamines and conformationally restricted polyamines. These different categories of agents may act by one or more different mechanisms to protect normal epithelial cells from the detrimental side effects of chemotherapeutic agents and radiation therapy. These mechanisms include, but are not limited to: (1) inhibiting cell division by depleting cells of natural polyamines, via inhibiting biosynthetic enzymes, inhibiting cellular uptake or activating catabolic enzymes; (2) acting as cellular or DNA protectors via scavenging of free radicals or other reactive species; (3) protecting cellular DNA by displacing natural, cellular polyamines and avidly binding to DNA, thus changing its shape and condensation; and (4) inhibiting cell division by altering the conformation of cellular DNA, thus, triggering the induced expression of surveillance proteins, thereby stimulating cell cycle arrest The inventors have demonstrated that representatives of each of the categories of polyamine effectors described above can confer this protective effect. For instance, the polyamines spermine, putrescine, norspermidine, cadaverine and spermidine, in at least one concentration tested, reduced or prevented cytoxan-induced alopecia or radiation-induced dermatitis in rats (Examples 1 and 2). Likewise, the polyamine biosynthetic pathway intermediates or inhibitors, agmatine, NG-hydroxy-arginine (NOHA), N1-N11-bis (ethyl) norspermine (BE-3-3-3) and DL-alpha difluoromethylornithine (DMFO) had some effect in reducing or preventing chemotherapy-induced alopecia or radiation-induced dermatitis in at least one concentration tested (Example 1 and Example 2). Similarly, the simple polyamine analogs SL-11122, 11103, 11141, 11102, 11095, 11038, 11050, 11101, 11104 and 11092 (structures set forth in one or more of U.S. Pat. No. 5,889,061, Valasinas et al., 2001, supra, WO 00/66587 and WO 02/38105) showed efficacy in the rat alopecia and/or dermatitis model, when tested at a concentration of 5 mM (Examples 6, 7 and 8). The long-chain polyamine analogs SL-11144, 11158, 11159 and 11160, and the constrained polyamine analogs SL-11047, 11093, 11094 and 11099 (structures set forth in one or more of U.S. Pat. No. 5,889,061, Valasinas et al., 2001, supra, WO 00/66587 and WO 02/38105) showed overall greater activity than did the naturally-occurring polyamines or simple polyamine analogs in both the alopecia and dermatitis models, when tested at 5 mM (Examples 6, 7 and 8). Certain of these compounds were also shown effective in a rat alopecia model wherein the chemotherapeutic agent was changed from cytoxan to cytarbine or doxorubicin (Example 8).

Thus, any polyamine, simple polyamine analog, long-chain polyamine analog, constrained polyamine analog or modulator of polyamine biosythesis, catabolism or transport is considered suitable for use as a polyamine effector in the present invention. In various embodiments of the invention, the polyamine effector is a naturally occurring polyamine, an intermediate in the polyamine biosynthetic pathway, or an analog that acts as a modulator of enzymes involved in polyamine biosynthesis, degradation or transport. Polyamine effectors that can be employed include common and/or naturally occurring polyamines found in prokaryotes and eukaryotic cells. Such compounds are known in the art (e.g., Morgan D. M. L., 1999, Molecular Biotechnology 11: 229). Specific examples include, but are not limited to: putrescine, spermidine, spermine, diaminopropane, cadaverine, norspermidine, aminopropylcadaverine, homospermine, norspermine, thermospermine, aminopentylnorspermidine, bis(aminopropyl)cadaverine, aminopropylhomospermine, canavalmine, homospermine, caldopentamine, aminopropylcanavaline, bis(aminopropyl) homospermidine, bis(aminobutyl)norspermidine, aminobutylcanavalmine, aminopropylhomospermine, homopentamine, N5-aminobutylhomospermine, caldohexamine, thermohexamine, homothermohexamine, agmatine and N6-methylagmatine. Polyamine effectors that are small molecule inhibitors or modulators of key enzymes in the polyamine biosynthetic pathway include, but are not limited to: ODC inhibitors such as difluoromethylornithine (DFMO), alpha-monofluoromethylornithine (MFMO), and methyl-acetylenicputrescine (MAP); AdometDC inhibitors such as S-(5-deoxy-5-adenoxyl)methylthioethylhydroxylamine (AMA), 5-deoxy-5-[(2-aminooxyethyl)methyl-lamino]adenosine (MAOEA), and methylglyoxal bis(guanylhydrazone) (MGBG); spermidine synthase inhibitors such as S-adenosyl-1,8-diamino-3-thiooctane (AdoDATO), cyclohexylamine, and butylamine; spermine synthase inhibitors such as S-adenosyl-1,12-diamino-3-thio-9-aza-dodecane (AdoDATAD) and N-(n-butyl)-1,3-diaminopropane (BDAP).

In a preferred embodiment of the invention, the polyamine effector is a polyamine or arginine analog that carries a functional group that confers a cellular or DNA protective effect to the molecule, or that modulates the polyamine biosynthetic or catabolic pathway. Compounds of this nature include, but are not limited to amifostine, NGhydroxy-arginine (NOHA), N1,N11-bis(ethyl) norspermine (BE-3-3-3), N12-bis(ethyl)spermine (BE-3-4-3), N,N-bis[3-(ethylamino)-propyl]-1,7-heptanediamine (BE-3-7-3), BE-3-3-3, BE-3-4-3, BE-3-7-3,N1-ethyl-N11-propargyl 4,8-diazaundecane, and the analogs SL-11141 and SL-11050 (structures set forth in one or more of U.S. Pat. No. 5,889,061, Valasinas et al., 2001,supra, WO 00/66587 and WO 02/38105).

In another preferred embodiment, the polyamine effector is a long-chain polyamine analog. Such polyamine effectors include, but are not limited to, analogs SL-11144, SL-11158, SL-11159 and SL-11160 (structures set forth in one or more of U.S. Pat. No. 5,889,061, Valasinas et al., 2001,supra, WO 00/66587 and WO 02/38105).

In another preferred embodiment, the polyamine effector is a conformationally restricted polyamine analog. Such polyamine effectors include, but are not limited to, analogs SL-11038, SL-11092, SL-11094, SL-11095, SL-11101, SL-11102, SL-11103, SL-11104, SL-11105, SL-11122, SL-11047, SL-11093 and SL-11099 (structures set forth in one or more of U.S. Pat. No. 5,889,061, Valasinas et al., 2001,supra, WO 00/66587 and WO 02/38105).

Additional specific examples of suitable polyamine effectors that can be employed in the compositions and methods of the invention are described in the following patents and publications, the contents of which, as mentioned previously, are incorporated by reference herein.

U.S. Pat. No.: 4,935,449, issued 19 Jun. 1990, to Bey, et al;
U.S. Pat. No.: 5,091,576, issued 25 Feb. 1992, to Bergeron;
U.S. Pat. No.: 5,109,024, issued 28 Apr. 1992, to Prakash, et al;
U.S. Pat. No.: 5,217,964, issued 8 Jun. 1993, to Edwards, et al;
U.S. Pat. No.: 5,354,782, issued 11 Oct. 1994, to Edwards, et al;
U.S. Pat. No.: 5,434,145, issued 18 Jul. 1995, to Edwards, et al;
U.S. Pat. No.: 5,654,484, issued 5 Aug. 1997, to Prakash, et al;
U.S. Pat. No. 5,648,355, issued 15 Jun. 1997, to Theoharides;
U.S. Pat. No.: 5,677,350, issued 14 Oct. 1997, to Frydman;
U.S. Pat. No.: 5,679,682, issued 21 Oct. 1997, to Bergeron;
U.S. Pat. No.: 5,681,837, issued 28 Oct. 1997, to Bergeron;
U.S. Pat. No.: 5,753,714, issued 19 May 1998, to Stemerick, et al;
U.S. Pat. No.: 5,827,894, issued 27 Oct. 1998, to Bergeron;
U.S. Pat. No.: 5,866,613, issued 2 Feb. 1999, to Bergeron;
U.S. Pat. No.: 5,889,061, issued 30 Mar. 1999, to Frydman, et al;
U.S. Pat. No. 5,994,339, issued 30, Nov. 1999, to Crapo, et al;
U.S. Pat. No.: 6,034,139, issued 7 Mar. 2000, to Bergeron;
U.S. Pat. No.: 6,114,394, issued 5 Sep. 2000, to Edwards, et al;
U.S. Pat. No.: 6,147,262, issued 14 Nov. 2000, to Bergeron;
U.S. Pat. No.: 6,172,261 B1, issued 9 Jan. 2001, to Vermeulin;
EP 0 162 413 A2, publication date 27 Nov. 1985;
EP 0 270 349 B1, publication of grant of patent 4 Aug. 1993;
EP 0 277 635 B1, publication of grant of patent 5 Jan. 1994;
EP 0 311 068 B1, publication of grant of patent 30 Mar. 1994;
EP 686,142 B1, publication of grant of patent 30 Dec. 1998;
EP 884,046 A1, publication date 16 Dec. 1998;
EP 1 085 011 A1, publication of grant of patent 21 Mar. 2001;
PCT WO 93/18760, international publication date 30 Sep. 1993;
PCT WO 94/07480, international publication date 14 Apr. 1994;
PCT WO 94/19311, international publication date 1 Sep. 1994;
PCT WO 96/23490, international publication date 8 Aug. 1996;
PCT WO 99/51213, international publication date 14 Oct. 1999;
PCT WO 00/16763, international publication date 30 Mar. 2000;
PCT WO/00/46187, international publication date 10 Aug. 2000;
PCT WO 00/66587, international publication date 9 Nov. 2000;
PCT WO 01/72685, international publication date 4 Oct. 2001; and
PCT WO/02/38105. international publication date 16 May 2002.

Examples of specific suitable polyamine effectors also are set forth in the following articles, the contents of which, as mentioned previously, are incorporated by reference herein.

"Conformationally Restricted Analogues of $^1$N,$^{12}$N-Bisethylspermine: Synthesis and Growth Inhibitory Effects on Human Tumor Cell Lines" by Reddy, et al. J. Med. Chem. 1998, 41: 4723–4732;

"Two polyamine analogs (BE-4-4-4 and BE-4-4-4-4) directly affect growth, survival, and cell cycle progression in two human brain tumor cell lines" by Bergeron, et al., Cancer Chemother Pharmacol 1995, 36: 411–147;

"Conformationally Restricted Analogues of $^1$N,$^{14}$N-Bisethylhomospermine (BE-4-4-4): Synthesis and Growth Inhibitory Effects on Human Prostate Cancer Cells" by Valasinas et al. J. Med. Chem. 2001,44: 390–403; and "Cis-Unsaturated Analogues of 3,8,13,18,23-Pentaazapentacosane (BE-4-4-4-4): Synthesis and Growth Inhibitory Effects on Human Prostate Cancer Cell Lines" by Reddy et al., J. Med. Chem. 2001,44: 404–417.

B. Compositions for Delivery of Polyamine Effectors:

Advantageously, because polyamine molecules as a family share the common characteristic of having multiple positive charges, they do not easily enter the bloodstream via "transdermal" delivery (i.e., crossing epidermis and dermis to achieve vascular distribution); however, the inventors have discovered that they are very well suited for topical "dermal" or "intradermal" delivery to specifically protect (1) the epidermal and hair follicle cells in the scalp or other skin, and (2) epithelial and mucosal cells lining the oral and gastrointestinal tract, from chemotherapeutic agents and radiotherapy. Inefficient transdermal delivery reduces systemic delivery of the polyamine analogs, thereby minimizing or eliminating unwanted exposure of major organs or tumor cells themselves to the polyamine effectors. Thus, the invention achieves efficient dermal/intradermal delivery and avoids systemic delivery of the active polyamine compounds. This is important for two reasons. First, it eliminates the possibility that the polyamine effectors will interfere with systemically administered chemotherapy by exerting a protective effect on the cancer cells. Second, it minimizes the likelihood that systemic distribution of the polyamine analog will cause significant toxic side effects to major organ systems, as has been observed.

The polyamine effectors are administered topically (or locally) to protect patients from the side effects of cancer therapy. The term "topical" denotes the administration of a drug intended to act locally rather than systemically. In the present invention, "topical" or "local" delivery is directed to epidermal and dermal cells of the skin and scalp (including cells lining hair follicles), as well as mucosal cells of the mouth, salivary glands, throat, gastrointestinal system and urogenital tract. For some of these latter locations, compositions may be formulated for oral or nasal delivery, or as suppositories. The goal of such delivery systems is to contact these internal surfaces topically with the polyamine effectors.

The local delivery of organic and biological substances within the skin or mucous membranes using a noninvasive delivery system has many attractions, including patient acceptability due to the noninvasiveness of the procedure, avoidance of gastrointestinal digestion and disturbances, and first-pass metabolism of the delivered molecule. Importantly, this route of administration is key for the delivery of compounds to protect skin (dermal) or mucosal surfaces from cancer therapy. Topical delivery is exploited in the present invention because it is not an efficient means for systemic drug delivery. It is estimated that only between 1%–5% of a drug in most topical formulations is systemically bioavailable.

In preferred embodiments of the invention, less than 10%, preferably less than 5% and most preferably less than 1% of the polyamine effector, provided topically e.g., dermal, intradermal, mucosal or GI epithelial delivery, move to reach the dermis and/or other underlying tissues.

Dermal delivery systems. Dermal delivery systems typically consist of the drug, prepared as solutions, emulsions or creams, ointments, gels or liposomes. The description, composition, production, and applicability of these major types of dermal delivery forms are set forth below.

The skin is a complex multiplayer organ with a total thickness of 2–3 mm. Skin consists of two main layers, the dermis and epidermis. The dermis provides physiological support for the epidermis and consists of connective tissue, nerves blood and lymph vessels, sebaceous and sweat glands. Epidermis is about 100 um thick and consists of a number of layers. The stratum germinativum is the basal layer for the epidermis. Above the basal layer are the stratum spinosum, the stratum granulosum, the stratum lucidum, and finally the stratum corneum. Each layer is in different stages of differentiation; during this differentiation the cells migrate from the basal layer to the surface and cornify to form the stratum corneum. The stratum corneum or the horny layer consists of flattened keratin-filled cells. A lipid matrix of the stratum corneum is formed of double-layered lipid membranes composed of cholesterol, free fatty acids and ceramides. The stratum corneum and the lipid matrix layer are primarily responsible for the low penetration rate of most topically delivered substances. Although this region is considered to be the main barrier to percutaneous absorption, it is also regarded as the main pathway for penetration. Therefore, compounds that loosen or fluidize the lipid matrix of the stratum corneum may enhance the permeation of substances through the skin. This is usually achieved by utilizing carrier molecules such as alcohols, albumin conjugates, lecithins, glycoproteins, polysaccharides and liposomes.

The skin also contains several other structures within the dermis, such as sebaceous (oil) glands, ecorine (sweat glands), and hair follicles. While the majority of the hair follicle exists within the dermal layer, the follicle itself is surrounded by epidermis. The follicle consists of an outer basement layer and an outer and inner root sheath that surrounds the hair shaft. At the base of the hair follicle, both the matrix cells and the dermal papilla together produce the hair shaft. The hair follicle has a three-phase life cycle. The anagen phase is the period in which the lower part of the follicle begins to produce hair. Since the matrix cells are rapidly dividing at this phase, these cells are very sensitive to the effects of cancer therapy. The catagen phase occurs next, in which the cells in the lower part of the follicle (matrix, dermal papilla), degenerate and die, and the hair shaft loses its mooring. The telogen phase follows next, in which the hair follicle is in a resting phase. As a normal part of the hair cycle, the hair shaft typically falls out in this phase.

Solutions are the most traditional types of formulations for topical dermal drugs, where the agent is solubilized in a solvent. Solvent-based systems are simple and effective constituents of topical delivery vehicles for some drugs. Alcohols are the most commonly used solvents for topical solutions. Typically, the drug is combined into a water and alcohol mixture. The alcohol content varies between 10–100%. Alcohols used include ethanol, propylene glycol, polyethylene glycols, methanol, or butanediol. Each of these types of alcohols is suitable for use in the present invention; others not listed are also suitable, as would be understood by one of skill in the art. High alcohol content solutions such as solutions of 70% ethanol in water or ones containing 60% ethanol, 20% propylene glycol and 20% water, are particularly good at penetrating the stratum corneum of the epidermis. Topical minoxidil, a hair regrowth treatment, uses the latter formulation as the delivery vehicle.

Solution-based delivery systems are ideal for the delivery of small organic molecules. In a preferred embodiment of the invention, particularly for administration of polyamine effectors to the epidermis, alcoholic solutions are particularly well suited. An aqueous alcohol-based delivery vehicle was proven effective for topical administration of polyamine effectors. Advantages of this delivery system include ease of manufacturing, fast drying, and ease of analysis of active drug compound after formulation. Solution-type formulations are typically administered using dropper bottles, in towlettes, or as aerosols.

Emulsions form the basis of cream and lotion type formulations. Typically, these formulations are colloidal dispersions composed of two immiscible phases; an oil phase and an aqueous phase with an emulsifier. Typical oils used in emulsions include stearyl alcohol, isopropyl lanolate, isopropyl myristate, cetyl alcohol, and vitamin E. Emulsifiers are essentially surfactants that lower the surface tension of the immiscible phases. Most emulsifiers tend to be fatty acid esters or stearates of glycerol, sorbitan, or polyoxyethylene (POE). Depending on the location of the oil and water, emulsions are oil-in-water, water-in-oil or combinations thereof. The preparation of an emulsion commonly requires some mechanical shear force with heat to mix the internal and external phases. Most topical emulsions contain viscosity builders such as natural gums (alginates, carrageenan, tragacanth, pectin, xanthan or collagen) at 1–5% to thicken the preparation. Higher percentages of viscosity builders produce creams, a lower percentage form lotions. Complete formulations for emulsions (creams and lotions) generally include water, alcohol, propylene glycol, sodium lauryl sulfate and white wax. In alternative formulations, they include water, alcohol, glycerol, phosphatidyl choline, lysophosphatidyl choline and triglycerides. In other embodiments of the invention, particularly for administration of polyamine effectors to the epidermis, emulsions are particularly well suited. Ease of administration, good local retention and slow release of drug are some of the attractive characteristics of emulsions for a topical delivery system.

All ingredients listed above for preparation of emulsions are suitable for use in the present invention, as well as any other such ingredients typically employed by one skilled in the art for such purpose.

Ointments are composed of fluid hydrocarbons meshed in a matrix of higher melting solid hydrocarbons. The hydrocarbon ointment base is typically petrolatum and white ointment. Ointments are prepared by melting the base, followed by the addition of excipients, such as antioxidants to the fluid. The drug is then suspended into the ointment by milling. Due to the high oil content, ointments tend to be greasy. Adding components, such as microcrystalline cellulose, which gives the ointment a dry feel on the skin, can reduce greasiness. A preferred embodiment includes a polyamine effector compound formulated as an ointment, utilizing any ingredient typically used for the preparation of ointments, as would be appreciated by one of skill in the art.

Gels are semisolids consisting of a gelling agent that is penetrated with liquid solvent. The concentration and the molecular weight of the gelling agent affect the consistency of vehicle formulation. The gelling agent is a suspension of either large organic or small inorganic molecules. The large organic molecules consisting of either natural or synthetic polymers exist as randomly coiled chains that entangle and form the gel structure. Some common polymers of this kind are natural gums, cellulose derivatives and acrylic acid polymers. Another class of these gels, called thermally sensitive gels, is prepared from poloxamers. In contrast, the small inorganic molecules form the gel structure by forming a somewhat organized three-dimensional network. Common small inorganic polymers include colloidal solids found in silica and clays. The nature of the solvent determines whether the gel is a hydrogel (water-based) or an organogel (non-aqueous solvent based). The viscosity of gels decreases upon application of shear forces (mixing or squeezing from a tube) or increases in temperature. A preferred embodiement includes various formulations of a polyamine effector compound within a gel. The property of gels overall are attractive for a topical delivery vehicle because they are relatively easy to prepare and tend to have a long residence time at the site of application allowing the slow release of compound at the desired site. All ingredients listed above for preparation of gels are suitable for use in the present invention, as well as unlisted ingredients typically employed by one skilled in the art for such purpose.

Liposomes are vesicles consisting of amphipathic lipids arranged in one or more concentric bilayers. When lipids are placed in aqueous medium, the hydrophilic interaction of the lipid head groups with water results in the formation of multilamellar and unilamellar systems or vesicles which resemble biological membranes in the form of a spherical shell. Liposomes may be small (0.025–0.05 um) to large multilamellar vesicles (0.05–10 um). Lipids used to prepare the liposomes include phospholipids, sphingolipids, glycosphingolipids, saturated glycerides, steroids (e.g., cholesterol) and synthetic phospholipids. Liposomes are typically prepared by melting the lipid together in aqueous solvent with an emulsifier like POE. The drug is then added and the liposomes are generated through mixing or sonication. The drug is usually entrapped in the vesicle structure. These basic liposomes are sometimes referred to as "conventional liposomes." Several other types of liposomal preparations exist, including (1) sterically stabilized liposomes, which are surface coated with an inert hydrophilic polymer, such as polyethylene glycol; (2) targeted liposomes, to which are attached targeting ligands, such as antibodies or fragments thereof, lectins, oligosaccharides or peptides (as discussed below, choleratoxin B (CTB) is used to target liposomes to the gastrointestinal epithelium); and (3) reactive or "polymorphic" liposomes, which change their phase and structure in response to a particular interaction (this group includes liposomes sensitive to ions (pH, cations), heat and light, among other stimuli.

Liposomes are good vehicles for dermatological applications. Liposomal delivery offers several advantages over more conventional formulations. The major advantages are: (1) reduced serious side effects and incompatability from undesirably high systemic absorption; (2) significantly enhanced accumulation of the delivered substance at the site of administration due to high compatability of liposomes with stratum corneum; (3) ready incorporation of a wide variety of hydrophilic and hydrophobic molecules into the skin; (4) protection of the entrapped compound from metabolic degradation; and (5) close resemblance to the natural membrane structure and their associated biocompatibility and biodegradability. All ingredients listed above and for preparation of various types of liposomes are suitable for use in the present invention, as well as any other such ingredients typically employed by one skilled in the art for such purpose.

In order to achieve efficient delivery of a polyamine effector molecule into the skin a preferred embodiment includes various formulations of liposomes (phospholipid-based vesicles, cationic liposomes, nonionic liposomes, non ionic/cationic liposomes, pegylated liposomes, PINC polymer, and propylene glycol and ethanol mixture (commonly used vehicle for administering minoxidil), and nonionic liposome/propylene glycol and ethanol mixtures. Reactive liposomes may be preferred for other embodiments of the present invention. Inclusion of cationic amphiphiles as a minor component of liposomes facilitates the association with negatively charged solutes, the rapid binding of liposomes to the cell surface, and the cellular uptake of liposomes. pH-sensitive liposomes have been developed to improve the efficiency of the cytoplasmic delivery of anti-tumor drugs, proteins, and nucleic acids. Most pH-sensitive liposomes have been prepared using phosphatidylethanolamine (PE). PE alone does not form liposomes and is prone to form the inverted hexagonal phase (HII). However, liposomes can be prepared by adding another bilayer-stabilizing, amphiphilic lipid component to PE. Titratable amphiphiles having a carboxyl group have been used as a component for the preparation of pH-sensitive liposomes. Because the ability to stabilize a bilayer membrane by these titratable amphiphiles decreases under acidic conditions, destabilization results in the fusion of the liposomes. pH sensitive liposomes are stable at physiological pH, and are internalized by cells through an endocytic pathway, which exposes the liposomes to an acidic pH. Liposomes within the endosome are destabilized and possibly fuse with the endosome membrane, resulting in release of their contents into the cytoplasm without degradation by lysosomal enzymes.

In other embodiments of the invention, sterically stabilized, inert liposomes are particularly suitable. In still other embodiments, targeted liposomes may be used to advantage.

Mucosal delivery systems. Mucosal delivery defined here is the local delivery of polyamine effectors to the mucosa of the mouth, GI, and urogenital tract. Mucosally active drugs, can be formulated as either solutions, emulsions or creams, ointments, gels or liposomes using the ingredients described above. In addition, there are also special excipients specifically designed for mucosal delivery. The description, composition, and applicability of these major types of mucosal delivery forms are set forth below. Each is considered suitable for practice of various embodiments of the present invention.

In general, the structure of the mucosal surface is composed of an outermost layer of stratified squamous epithelium, below which lie a basement membrane, a lamina propria followed by the submucosa as the inner-most layer. The mucosae of areas subject to mechanical stress such as the gingivae or the hard palate are also keratinized, similar to the epidermis. Depending on the keratinization, the mucosa is somewhat permeable. The permeability of oral mucosa is 4–4000 times greater than that of the skin. Permeability of intestinal mucosa is even greater. The cells of the epithelia are surrounded by an intercellular ground substance, mucous, the principal components of which are complexes of proteins, carbohydrates, lipids and ceramides. Primarily, special mucous-secreting cells, called goblet cells, synthesize mucous. However, in the oral mucosa, most of the mucous is produced by the major and minor salivary glands. Mucous forms a strongly cohesive gel structure that will bind to the epithelial cell surface as a gelatinous layer. The penetration of this mucous layer and the local retention of compound because of its permeability must be achieved for effective mucosal drug delivery. However, this route of administration is very important for the delivery of compounds designed to protect mucosal surfaces from cancer therapy. Since the mucosal surface is a common site in which many of the unwanted side effects occur, the use of formulated mucosally-active drugs designed to prevent these effects, makes sense.

One challenge associated with efficient mucosal delivery is low flux or drug transport through the mucous layer. Poor retention and bioadhesion at the mucosal site should also be considered. Both result in low drug bioavailability within the mucosal tissues. Much of the work in this area has focused on the use of mucosal permeation enhancers to promote drug flux and mucoadhesives, which improve drug retention.

Mucosal permeation enhancers are designed to improve drug flux or penetration at the mucosal surface. The use of these enhancers can increase drug permeability by 100-fold or more. Various permeation/absorption enhancers vary in molecular weight and physicochemical properties. In a preferred embodiment for mucosal delivery, permeation enhancers are included in formulations for polyamine effector delivery to the mucosal surface. Most types of enhancers are detergents that include: sodium glycocholate, sodium taurocholate, polysorbate 80, sodium lauryl sulfate, lauric acid, and various alkyl glycosides. Other examples of enhancers include: dextrins (cyclodextrin, dextran sulfate), fatty acids (phosphatidylcholine, lysophosphatidylcholine), heterocyclic compounds (azone), and small molecules (benzalkonium chloride, cetyltrimethylammonium bromide). Each is contemplated for use in the present invention as are other unlisted ingredients typically used for such purpose, as would be appreciated by one of skill in the art.

Another issue to be addressed to achieve effective mucosal delivery is the lack of retention at the site of absorption. The addition of mucoadhesives to the formulation can improve local retention of mucosally delivered compounds. In another preferred embodiment for mucosal delivery, mucoadhesives are included in the polyamine effector formulations of the invention. Mucoadhesive compounds are primarily synthetic or natural polymers that can adhere to the wet mucosal surface. These include synthetic polymers such as monomeric alpha cyanoacrylate, polyacrylic acid, hydroxypropyl methylcellulose, and poly methacrylate derivatives. Glue-like polymers include epoxy resins and polyurethanes. Naturally occurring mucoadhesives include chitosan, hyaluronic acid and xanthan gum. Each is contemplated for use in the present invention as are other unlisted ingredients typically used for such purpose, as would be appreciated by one of skill in the art.

Other delivery vehicles are also suitable for use in the present invention, particularly for administration of polyamine effectors to the mucosa and lumen of the GI and urogenital tract. Nonlimiting examples include: (1) oils such as vegetable oils or fish oils (which can be encapsulated into standard gel capsules); and (2) emulsions prepared, for example, by dispersing polyoxyethylene ethers, e.g., 10-stearyl ether (Brij 76) in aqueous buffer.

Other examples of delivery vehicles suitable for the GI or urogenital mucosa include biodegradable microparticles (preferably in the range of 0.1–10 uM diameter) of polylactic polyglycolic acid, which have been used to deliver proteins to Caco-2 cells as an in vitro model system for gastrointestinal uptake via oral drug delivery (Desai et al., Pharm. Res. 14: 1568–1573, 1997). Significant uptake of proteins carried by polystyrene particles into cells lining the small intestine of the rat has been demonstrated (Hillery et al., J. Drug Targeting 2: 151–156, 1994). Indeed, delivery of protein-containing microparticles has been reported from the GI lumen all the way to the submucosal vasculature (Aphramaian et al., Biol. Cell 61: 69–76, 1987). Therefore, such polymeric microparticles are quite suitable for oral delivery of polyamine effectors to gastrointestinal epithelial cells, which are found on the surface of the GI lumen.

C. Administration of Compositions Comprising Polyamine Effectors:

Depending on the cell population or tissue targeted for protection, the following sites of topical administration of the compositions of the invention are contemplated: oral, nasal, ophthalmic, gastrointestinal, urogenital and dermal (cutaneous). Because targeted delivery is contemplated, certain of these modes of administration are most suitable for targeted delivery vehicles (e.g., CTB- or antibody-studded liposomes).

The compositions of the present invention are generally administered to a patient as a pharmaceutical preparation. The term "patient" as used herein refers to human or animal subjects (animals being particularly useful as models for clinical efficacy of a particular composition). Selection of a suitable pharmaceutical preparation depends upon the method of administration chosen, and may be made according to protocols well known to medicinal chemists.

The pharmaceutical preparations comprising the compositions of the invention are conveniently formulated for administration with a biologically acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of a particular composition in the chosen medium will depend on the hydrophobic or hydrophilic nature of the medium, in combination with the specific properties of the delivery vehicle and active agents disposed therein. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional medium or agent is incompatible with the compositions to be administered, its use in the pharmaceutical preparation is contemplated.

Formulations for topical administration may contain a variety of excipients that function to stabilize and solubilize the drug formulation, increase permeation, and protect and aid in the application to the skin. Oil or water-based excipients are primarily added to improve drug solubility and spreadibility to the formulation. Surfactants may be added to topical formulations as detergents, solubilizers, emulsifiers, and wetting agents. Topical formulations often require preservatives and anti-microbial agents. Commonly used anti-microbial preservatives include but are not limited to: alcohols, quaternary amines, acids, parabens, and phenols. Other types of preservatives are designed to prevent the oxidation of the drug and excipient. This can occur either by auto-oxidation due to presence of free radicals or by photo-oxidation. Some antioxidants that include ascorbic acid, sodium metabisulfite, and thiourea function because they are preferentially oxidized over the drug. Others such as tocopherols and butylated hydroxyanisole are oxidation propagation terminators. Since the presence of trace amounts of metals can result in auto-oxidation, chelating agents are also added as preservatives. For dermal delivery, humectants and emollients may be added to the formulation.

Both humectants and emollients are found in most moisturizers. Humectants help increase the water content of the top layers of skin. Emollients help maintain a soft, smooth pliable skin by acting as a lubricant. Commonly used humectants in dermatology are glycerin and propylene glycol. Petrolatum, lanolin, mineral oil, and isopropyl myristate are examples of emollients. Some emollients, such as lactic acid, urea, and allantoin, act by chemically altering the keratin layer to soften the skin. Other special types of excipients may be required to be added to the topical formulation. These include: skin protectants (zinc oxide, glycerin, dimethicone) emulsion stabilizers (cellulose polymers, carbomer resins) and pH adjusters.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of the polyamine effector calculated to produce the desired protective effect in association with the selected pharmaceutical carrier. Procedures for determining the appropriate dosage unit are well known to those skilled in the art.

Dosage units may be proportionately increased or decreased based on the weight and/or body surface area of the patient. Appropriate concentrations for achieving protection of a target cell population or tissue from the toxic effect of a particular chemotherapeutic agent may be determined by dosage concentration curve calculations, as known in the art.

As one example, for topical applications, the polyamine effector may be used at concentrations ranging from 0.1–250 mM, preferably 1–100 mM, in an appropriate carrier (e.g., alcohol solvent) applied to the scalp or other dermal site. This dosage is arrived at from results of experiments using a rodent model and the range of dosages is a function of results obtained from experiments using several different molecules that ranged in dose effectiveness. The volume of material applied to the skin ranges by size of surface area to be covered; e.g., scalp treatment for young children requiring 3–5 ml, the amount being increased in adults to 10–20 ml per application.

As another example, for gastrointestinal administration, the oral dose of the polyamine effector in an appropriate medium (e.g., solvent, liposome emulsion) is normalized to the lumenal surface area of the stomach and duodenum. This would assume that the patient consumes the material on an empty stomach upon rising in the morning.

It will also be appreciated by persons of skill in the art that pharmaceutical formulations of the invention may contain more than one polyamine effector agent. Various combinations of such agents may be useful for certain applications, and formulations of such combinations would be prepared according to the general guidelines set forth above. Moreover, one or more polyamine effector may be combined with other agents, such as other anti-proliferative agents or chemoprotective drugs, to provide a pharmaceutical formulation that is effective by two different modes of action. An anti-proliferative agent suitable for such use is the cyclin-dependent kinase II inhibitor described in PCT application US00/05186, published Dec. 28, 2000 as WO 00/78289 or genistein, an inhibitor of tyrosine protein kinase. A chemoprotective agent suitable for such use is resveratrol (trihydroxy-trans-stilbene). Further, certain of the chemoprotective inducing agents described herein also possess anti-proliferative activity. Several classes chemoprotective inducing agents that may be combined with the polyamine effectors of the invention are described in detail in commonly-owned, co-pending U.S. application Ser. No. 09/565,714, filed May 5, 2000, and International Application No. PCT US01/14464, filed May 4, 2001, the entireties of each of which are incorporated by reference herein.

Regimens for administration of pharmaceutical preparations. The pharmaceutical preparation comprising the compositions of the invention may be administered at appropriate intervals, before, during, or after a regimen of chemotherapy and/or radiotherapy. The appropriate interval in a particular case would normally depend on the nature of the chemotherapy or radiotherapy and the cell population targeted for protection.

For instance, for prevention of chemotherapy-induced alopecia, solvents, liposomes or other delivery vehicles containing the polyamine effector agents can be further formulated to be delivered, (e.g., as a topical solution, cream, or gel) to the scalp of a patient prior to scheduled administration of chemotherapy. By protecting the epithelial cells that line the exposed surface of hair follicles from the chemotherapy drug, the loss of hair commonly associated with cancer chemotherapy can be prevented. Likewise, for the treatment of radiation-induced dermatitis, the polyamine effector can be further formulated as a gel, ointment or cream containing moisturizers. This would help protect the epidermis from radiation damage. As described in greater detail in the examples, the topical formulation preferably is initiated several days prior to the cancer therapy, to ensure that the epithelial and mucosal cells are adequately treated. The formulation may then continue to be applied during the course of chemotherapy.

For protection of the gastrointestinal epithelium, the polyamine effector is formulated to be delivered by mouth to a patient prior to scheduled administration of cancer treatment. Administration of the protective formulation in the 1–5 days prior to radiotherapy or the infusion of the chemotherapeutic agent thus confers protection to susceptible mucosal epithelial cells. For example, the patient would be instructed to consume a "shake" containing the polyamine effector in an orally acceptable solution or liposome emulsion before breakfast in the morning, in the 1–5 days preceding chemotherapy. This would allow the polyamine effector to be present when the chemotherapy drugs or radiotherapy act on the GI mucosal epithelium. For protection of the lower GI tract, the composition may be administered in the form of a suppository.

Using animal models of chemotherapy-induced alopecia and radiation-induced dermatitis, the inventors have found that the topical application of certain natural polyamines, polyamine analogs or polyamine pathway inhibitors in an appropriate delivery vehicle can effectively reduce the severity of these unwanted side effects. Polyamine effectors were topically administered several days before and after either radiation or chemotherapy challenge. The ability to diminish the harmful side effects using the polyamine effectors was assessed using a scoring system to judge efficacy. Experimental methods and results are detailed in the following sections.

The following examples are provided to illustrate the invention. They are not intended to limit the invention in any way.

LIST OF TABLES FOR EXAMPLES

Table 1. Effect of topical treatment with natural polyamines on alopecia in rat pups challenged with cytoxan.

Table 2. Effect of agmatine in preventing alopecia in rat pups challenged with cytoxan.

Table 3. Effect of topical treatment with polyamine pathway analogs on alopecia in rat pups challenged with cytoxan.

Table 4. Topical treatment with polyamine analog BE-3-3-3 is effective against alopecia in rat pups challenged with cytoxan.

Table 5. Effect of topical treatment with polyamine biosynthetic inhibitors on alopecia in rat pups challenged with cytoxan.

Table 6. Effect of topical treatment with polyamine effectors on radiation-dermatitis in rats.

Table 7. Radiation-induced mucositis dose response.

Table 8. Effect of topical treatment with selected polyamine analogs on alopecia in rat pups challenged with cytoxan.

Table 9. Effect of topical treatment with selected polyamine analogs on dermatitis in rats exposed to radiation.

Table 10. Summary of alopecia scores for the cytoxan-induced alopecia model in rat pups treated with selected polyamine analogs Table 11. Summary of alopecia scores for the cytoxan-induced alopecia model in rat pups treated with polyamines from different structural families Table 12. Summary of alopecia scores for the cytarbine-induced alopecia model in rat pups Table 13. Summary of alopecia scores for the doxorubicin-induced alopecia model in rat pups Table 14. Summary of radiation dermatitis scores in the rat model challenged with 15 Gy radiation Table 15. Summary of alopecia scores for cytoxan-induced alopecia model in rat pups Example 1

Prevention of Chemotherapy-Induced Alopecia by Topical Application of Polyamine Effectors The inventors postulated that drug-induced alopecia could be reduced or prevented by selective protection of hair follicles. Specifically, the anti-proliferative effect of polyamine effector treatment would slow the growth of the hair follicle. Moreover, the DNA binding properties of certain subsets of polyamine effectors could provide protection of cellular DNA against reactive chemotherapy and radiotherapy by-products. Consequently, the hair follicle should become less susceptible to cancer therapy and alopecia should be diminished or eliminated. In this example, it is demonstrated that topically administered polyamine effectors were effective against chemotherapy-induced alopecia in a rat model of chemotherapy-induced alopecia. This animal model mimics many of the features found in chemotherapy-induced alopecia seen in humans and is considered a clinically relevant model for testing novel therapeutics.

Materials and Methods:

Induction of alopecia by cytoxan (CTX). Lactating Sprague Dawley mother rats with rat pups were purchased from Harlan Sprague Dawley (Indianapolis, Ind.). The mother rats were given food and water ad libitum. The rats pups were tested in the model of chemotherapy-induced alopecia described by Hussein A. M. et al., Science: 249, 1564 (1990). Cytoxan (CTX), a chemotherapeutic widely used in the treatment of cancer, was used to induce alopecia in the rats. A common side effect of cytoxan in patients is alopecia. Cytoxan and polyamine effector compounds were purchased from Sigma Chemicals Co. (St. Louis, Mo.). To produce CTX-induced alopecia, 7 to 10 day old rat pups were injected i.p. with 35 mg/kg of CTX prepared in phosphate-buffered saline. To produce reproducible CTX induced alopecia, we first tested several concentrations (35, 40, 45 ug/gm body weight) of CTX in phosphate-buffered saline (PBS), which was injected i.p. in 7–10 day old pups. Seven to ten days after CTX treatment the pups were examined to determine the degree of hair loss. The density of hair on the pups was then determined. 100% hair density represents that found on the untreated control pups while 0% represented pups with total hair loss. It was observed that 35 ug/gm of CTX was sufficient to induce 100% hair loss approximately 7 days after cytoxan challenge, and this concentration was used in subsequent experiments.

Different types of polyamine effector agents were tested in this model. The effectors were prepared in a delivery vehicle, consisting of from 60–100% ethanol in water, depending on the solubility of the compound. The compounds in ethanol/water solution from 50–150 µl in volume were topically administered to the backs of the pups once per day before and after CTX challenge. Using a micropipette, the formulation was applied to approximately 2 cm$^2$ section of skin to the backs of the rat pups. Specifically, the pups were treated once daily for the 4–5 days before CTX challenge, once on the day of CTX challenge and once daily for 5 days afterwards. Control groups consisted of pups receiving only delivery vehicle. Control groups treated with delivery vehicle were tested as part of every treatment study. Two or more animals were tested per group in both the control and test groups.

Approximately 7 to 10 days after CTX treatment, the pups were evaluated for alopecia. Hair loss was evaluated using a modified alopecia-scoring index described by Chen G. et al., Int. J. Cancer: 75, 303 (1998). A score of 0=no hair loss; a score of 1=10–30% hair loss; a score of 2=40–60% hair loss; a score of 3=70–90% hair loss; and a score of 4=100% hair loss.

Polyamine effectors tested. Different classes of polyamine effectors were tested using the chemotherapy-induced alopecia model. The classes fell under three categories: natural polyamines, analogs (of polyamines or arginine), and inhibitors of polyamine biosynthesis. The concentrations tested ranged from 0.08 mM to 100 mM.

| Compound | Concentrations tested (mM) |
| --- | --- |
| Natural polyamines | |
| Spermine | 100, 50, 20, 10, 4, 2, 0.8, 0.16 |
| Spermidine | 50, 10 |
| Norspermidine | 50, 5 |
| Putrescine | 50, 10, 5, 2 |
| Agmatine | 10, 1 |
| Cadaverine | 50, 5 |
| Analogs | |
| NG-hydroxy-arginine (NOHA) | 5 |
| N1, N11-bis (ethyl) norspermine (BE-3-3-3) | 20, 10, 5, 1 |
| Inhibitors of polyamine biosynthesis | |
| Alpha-Methyl ornithine | 20, 5 |
| DL-Alpha Difluoromethylornithine HCl (DFMO) | 20, 10, 5, 1 |

Results:

Natural polyamines. Results indicate that topical treatment using natural polyamines was effective at preventing alopecia caused by CTX. The results from the testing of natural polyamines are shown in Tables 1 and 2. Table 1 lists the results of the natural polyamines that were effective in the rat model of chemotherapy-induced alopecia. Spermine, putrescine, norspermidine, and cadaverine prevented hair loss in the rats after CTX challenge. Near complete hair retention was seen using some of the polyamines, such as spermine and putrescine, with alopecia scores of 0.0–1.5. Norspermidine, and cadaverine treatment at the concentrations shown reduced alopecia, with average alopecia scores of 2.0–2.5. In contrast, vehicle-treatment was consistently ineffective at preventing alopecia, and the pups treated with vehicle alone lost 100% of their hair after CTX challenge. Spermine was most effective at preventing hair loss, although the effects of putrescine were found to be more reproducible in these experiments. Table 1 also shows that a dose-dependent response was demonstrated in this model using the polyamines. Topical putrescine treatment of pups also produced a very consistent dose response. Interestingly, spermidine treatment at lower concentrations (10 mM) was more effective than higher concentrations (50 mM) in these experiments. Representative results are also shown in FIG. 1.

TABLE 1

| Treatment | Avg Alopecia Score* |
| --- | --- |
| Vehicle** | 4.0 |
| Spermine (100 mM) | 0.0 |
| Spermine (50 mM) | 2.0 |
| Spermine (20 mM) | 3.0 |
| Putrescine (50 mM) | 1.5 |
| Putrescine (10 mM) | 2.0 |
| Putrescine (5 mM) | 2.5 |
| Putrescine (2 mM) | 3.0 |
| Norspermidine (50 mM) | 2.0 |
| Norspermidine (5 mM) | 4.0 |
| Cadaverine (50 mM) | 2.5 |
| Cadaverine (5 mM) | 4.0 |
| Spermidine (50 mM) | 3.5 |
| Spermidine (10 mM) | 2.0 |

*Hair loss was determined using an alopecia scoring scheme (Chen G., et al.): 0 = no hair loss, 1 = 10–30% hair loss, 2 = 40–60% hair loss, 3 = 70–90% hair loss, and 4 = 100% hair loss.
**This control was re-run in every independent experiment.

The alopecia score result using agmatine is shown in Table 2. Agamatine, a early intermediate in the polyamine pathway, reduced, but did not prevent alopecia in this model.

TABLE 2

| Treatment | Avg Alopecia Score* |
| --- | --- |
| Vehicle** | 4.0 |
| Agmatine (10 mM) | 3.0 |
| Agmatine (1 mM) | 3.0 |

*Hair loss was determined using an alopecia scoring scheme (Chen G., et al.): 0 = no hair loss, 1 = 10–30% hair loss, 2 = 40–60% hair loss, 3 = 70–90% hair loss, and 4 = 100% hair loss.
** This control was re-run in every independent experiment.

Analogs. Results indicate that the analogs were effective at preventing alopecia caused by CTX. The results from several analogs are shown in Table 3.

TABLE 3

| Treatment | Avg Alopecia Score* |
| --- | --- |
| Vehicle** | 4.0 |
| NG-hydroxy-arginine (NOHA) (5 mM) | 2.75 |
| N1, N11-bis (ethyl) norspermine (BE-3-3-3) (20 mM) | 1.7 |
| BE-3-3-3 (5 mM) | 2.3 |
| (BE-3-3-3) (1 mM) | 2.7 |

*Hair loss was determined using an alopecia scoring scheme (Chen G., et al.): 0 = no hair loss, 1 = 10–30% hair loss, 2 = 40–60% hair loss, 3 = 70–90% hair loss, and 4 = 100% hair loss.
**This control was re-run in every independent experiment.

Both analogs, the arginine analog NOHA, and the alkylated polyamine analog, BE-3-3-3, which each act on the polyamine pathway in presumably at different sites, inhibited CTX from inducing alopecia. A dose reponse effect using 20 mM, 5 mM, and 1 mM was also seen using BE-3-3-3 (Table 3). As shown in Table 4, BE-3-3-3 treatment results were significant and the compound was consistently effective. Overall, BE-3-3-3 was an effective analog at preventing alopecia in this model.

TABLE 4

| Treatment | Alopecia Score* ±/SEM | | |
| --- | --- | --- | --- |
| | Expt. 1 | Expt. 2 | Expt. 3 |
| Vehicle | 4.0 +/− 0.0 | 3.5 +/− 0.7 | 4.0 +/− 0.0 |
| BE-3-3-3 (10 mM) | 1.5 +/− 0.7 | 0.25 +/− 0.3 | 2.0 +/− 0.3 |
| BE-3-3-3 (1 mM) | 3.5 +/− 0.7 | 2.5 +/− 0.3 | 2.7 +/− 0.4 |

*Hair loss was determined using an alopecia scoring scheme (Chen G., et al.): 0 = no hair loss, 1 = 10–30% hair loss, 2 = 40–60% hair loss, 3 = 70–90% hair loss, and 4 = 100% hair loss. Combined data of BE-3-3-3 at 10 mM was significant ($P < 0.01$) using Mann-Whitney U test.

Biosynthetic inhibitors. Results indicate that, at the concentration tested, certain polyamine biosynthesis inhibitors were effective at preventing alopecia caused by CTX. The results using several of these analogs are shown in Table 5. DFMO effectively prevented alopecia in the model at concentrations of 5–10 mM. A higher dose of DFMO (20 mM) was significantly less effective at protecting against alopecia. This may be due to the cytotoxic effect of high concentrations and/or an over anti-proliferative effect of DFMO on the hair follicle. Alpha-Methyl ornithine treatment did not prevent hair loss after CTX challenge in this model.

TABLE 5

| Treatment | Avg Alopecia Score* |
| --- | --- |
| Vehicle** | 4.0 |
| Alpha-Methyl ornithine (20 mM) | 4.0 |
| Alpha-Methyl ornithine (5 mM) | 4.0 |
| DL-Alpha Difluoromethylornithine HCl (DFMO) (20 mM) | 3.5 |
| DFMO (10 mM) | 2.0 |
| DFMO (5 mM) | 2.0 |
| DFMO (1 mM) | 4.0 |

*Hair loss was determined using an alopecia scoring scheme (Chen G., et al.): 0 = no hair loss, 1 = 10–30% hair loss, 2 = 40–60% hair loss, 3 = 70–90% hair loss, and 4 = 100% hair loss.
**This control was re-run in every independent experiment.

Overall, the inventors have demonstrated that treatment with polyamine effectors is able to effectively prevent alopecia in a chemotherapy-induced alopecia model. Furthermore, the inventors have shown that different members of each class (e.g. natural polyamines, analogs, biosynthetic inhibitors) of polyamine effector are effective in reducing or preventing chemotherapy-induced alopecia.

Example 2

Prevention of Radiation-Induced Dermatitis by Topical Application of Polyamine Effectors Materials and Methods:

To determine if treatment with a polyamine effector could effectively prevent radiation-induced dermatitis, adult rats were topically treated with several different classes of polyamine effectors before and after radiation treatment. Rats were exposed to medically relevant levels of radiation that could induce clinical radiation dermatitis. Sprague Dawley rats (Harlen Spraque Dawley) at 4–6 weeks-old were anesthetized with sodium pentobarbital at 40 mg/kg body weight (Sigma, St. Louis, Mo.) prior to radiation exposure. A defined, depilated area on the backs of rats was irradiated using a Mark I, Model 30, Cs 137 irradiator (J. L. Sheppard & Associates). Briefly, the back was stripped of hair to expose the skin using a 1:1 rosin/beeswax mixture. The rest of the body was protected from radiation exposure using a lead shield. A dose response study was initially preformed to reproduce relevant dermatitis that matched the Grade (I–IV) scale used to score the severity of radiation-induced dermatitis in the clinical setting. Radiation doses of 5–7 Gray (1 Gray (Gy)=100 mrem) produced Grade I dermatitis within 8–10 days. Radiation doses of 7–10 Gy produced Grade II dermatitis within 8–10 days. After 8–10 days, severe radiation dermatitis was produced at 20–25 Gy (Grade III dermatitis) or at 30–35 Gy (Grade IV). Radiation dermatitis of Grade II–III was considered most clinically relevant, so a radiation challenge dose of 15 Gy in the rats was used in subsequent treatment experiments. The stripped back region on the rats was treated topically with 10–50 mM polyamine effector once daily for 5 days before and 5 days after radiation challenge.

Different classes (natural polyamines and biosynthetic inhibitors) of polyamine effector agents were tested in this model. The polyamine effector compounds were purchased from Sigma Chemicals Co. (St. Louis, Mo.), except Vaniqa, a commercially available cream containing DFMO at 13.9% (63 mM). The effectors were prepared in a delivery vehicle, consisting of from 60–100% ethanol in water, depending on the solubility of the compound. The compounds in ethanol/water solution from 100–150 µl in volume were topically administered to the stripped region. Rats treated with only the delivery vehicle served as controls. Eight to ten days post-radiation challenge, the rats were evaluated for dermatitis using a modified scoring scale described by Masuda K. et al. Int. J. Radiation Oncol. Biol. Phys: 12, 1645 (1986). Dermatitis score of 0=normal, 1=slight redness, scaly skin with no focal lesions, 2=moderate redness, breakdown of larger area, some small focal lesions, 3=skin very red, breakdown of most of the irradiated area, large ulcers and crusty lesions, 4=skin very red, breakdown of the entire irradiated area, severe exudation and large crusty lesions.

Figure 2:
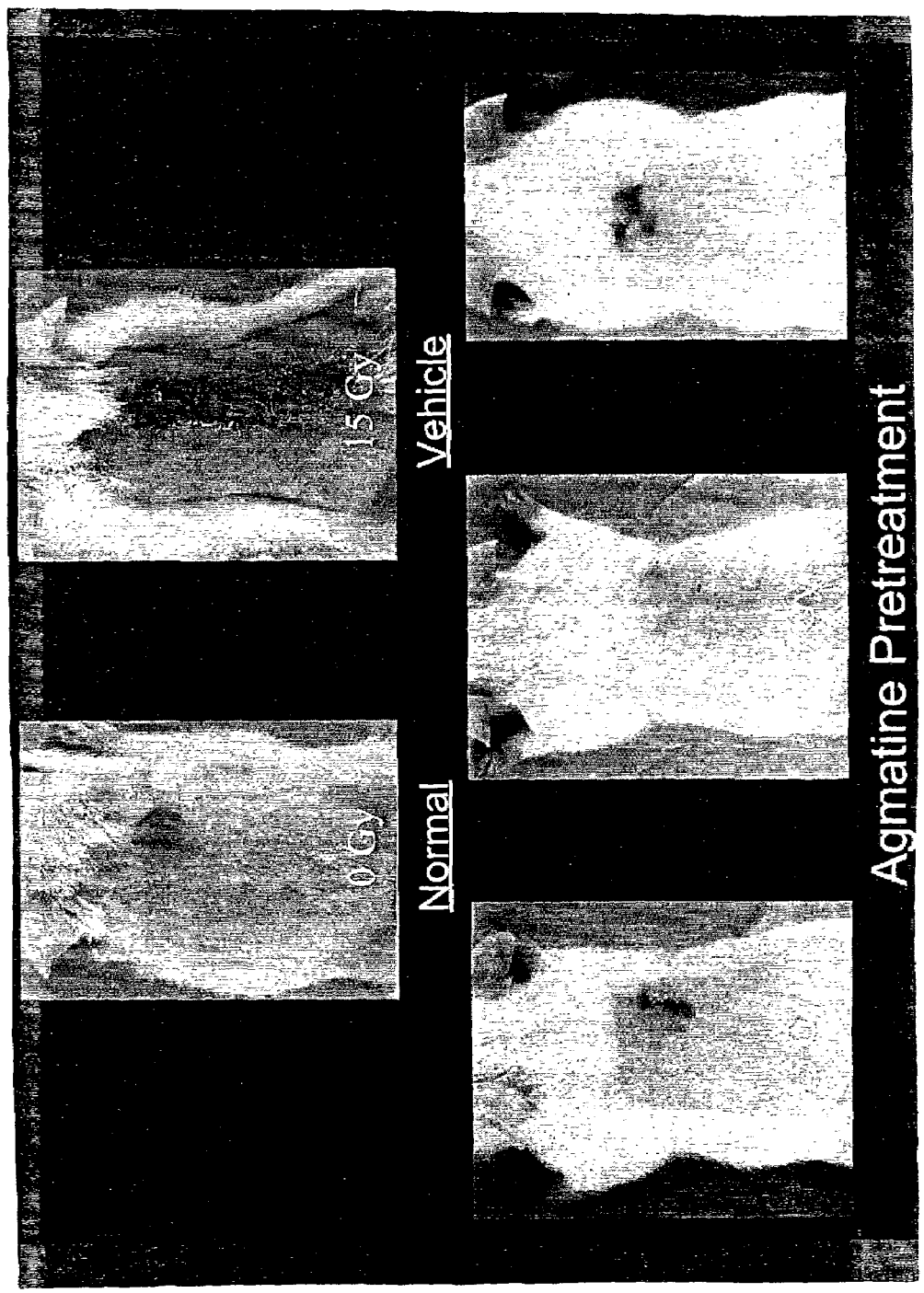
FIG. 2. Protection against radiation-induced dermatitis in rat model. A topical formulation containing either agmatine or vehicle alone was applied topically, once per day for 10 days to the shaved backs of the animals. Animals received a single dose of 15 Gy radiation on day 5 of the topical polyamine treatment. Treatments are marked in the panels.

Results:

Polyamine effectors were found to be effective at reducing or eliminating radiation-induced dermatitis in the rat. Results are shown in Table 6 and FIG. 2. Dermatitis scores of 3, or roughly equivalent to Grade III dermatitis were seen in the rats treated with only delivery vehicle. In contrast, topical treatment with several polyamine effectors effectively reduced the severity of the dermatitis. Agmatine was very effective, giving an average dermatitis score of 1.8. Spermine and DFMO at 10 mM were less effective. These results indicate that a topical polyamine effector such as agmatine can effectively reduce radiation-induced dermatitis. Interestingly, agmatine treatment was less effective at preventing chemotherapy-induced alopecia (Example 1) than at preventing radiation induced dermatitis. This may indicate that the mechanism of action of the polyamine effectors in the both models is different (e.g. activity by anti-proliferation as opposed to a nucleic acid protective effect).

TABLE 6

| Treatment | Avg dermatitis score* |
| --- | --- |
| Vehicle** | 3.0 |
| Agmatine (20 mM) | 2.0 |
| Agmatine (10 mM) | 1.8 |
| Putrescine (50 mM) | 3.0 |
| Spermine (50 mM) | 2.8 |
| DFMO (10 mM) | 2.5 |
| DFMO (Vaniqa) (63 mM) | 3.0 |

*0 = normal, 1 = slight redness, scaly skin with no focal lesions, 2 = moderate redness, breakdown of larger area, some small focal lesions, 3 = skin very red, breakdown of most of the irradiated area, large ulcers and crusty lesions, 4 = skin very red, breakdown of the entire irradiated area, severe exudation and large crusty lesions.
**This control was re-run in every independent experiment.

Example 3

Radiation-Induced Mucositis Model in Hamsters

Materials and Methods:

The model for radiation-induced oral mucositis was developed for the purpose of screening and identifying effective polyamines useful for treatment. The model used in this example was derived from the oral mucositis model described by Sonis S. T. et al. (Oral Oncology 36:373–381, 2000). Male golden Syrian hamsters (70–95 gram, 35–42 days, Charles River Laboratories, Wilmington, Mass.) were used. Animals were individually numbered, housed in small groups and fed and watered ad libitum. Hamsters were anesthetized with sodium pentobarbital (80 mg/kg body weight, Sigma, St. Louis, Mo.). The left buccal cheek pouch was everted and secured. A protective lead shield covered the remainder of the animal. Subsequently, the cheek pouch was irradiated with a single dose of radiation from 10 to 50 Gy delivered to the targeted mucosa in the 137 Cs Irradiator. Starting 10 to 12 days after radiation, the severity of mucositis was assessed every two days. The severity level of mucositis was evaluated using a modified mucositis scoring system described by Sonis S. T. et al. (Oral Oncology 36:373–381, 2000) The scoring system was as follows:

0=Pouch completely healthy. No erythema or vasodilatation.
1=Erythema.
2=Severe erythema, vasodilatation
3=Severe erythema and vasodilatation. Superficial erosion on radiated pouch surface area.
4=Formation of ulcers in one or more places. Cumulative ulcer formation about up to 50% of radiated pouch surface area. Diminished pliability of mucosa
5=Virtually more then 50% or complete ulceration of the radiated pouch mucosa. Loss of pliability.

Results:

Manifestations of radiation-induced mucositis were observed by day 12. The hamster buccal pouches were evaluated for the presence of mucositis and photographed every two days from day 12 to day 20. Mucositis was found to increase in severity, reaching a peak at day 16. An obvious dose response of radiation was seen, as shown in Table 7. In this experiment, the grades of mucositis at day 16 were scored as:

TABLE 7

| Treatment | Mucositis Grade* |
|---|---|
| 0 Gy | 0 |
| 10 Gy | 1 |
| 20 Gy | 2 |
| 30 Gy | 2.5 |
| 40 Gy | 4 |
| 50 Gy | 5 |

*0 = Pouch completely healthy. No erythema or vasodilatation, 1 = Erythema. 2 = Severe erythema, vasodilatation, 3 = Severe erythema and vasodilatation. Superficial erosion on radiated pouch surface area, 4 = Formation of ulcers in one or more places. Culmulative ulcer formation about up to 50% of radiated pouch surface area. Diminished pliability of mucosa, 5 = Virtually more then 50% or complete ulceration of the radiated pouch mucosa. Loss of pliability.

Thus, a reproducible model of radiation-induced mucositis in hamsters was successfully generated. This model is useful for investigating the efficacy of many classes of polyamine effector compounds for the treatment of radiation-induced mucositis.

Example 4

Identification of Liposome Carriers for Delivery of Polyamine Effectors to Epithelial Cells Materials and Methods:

In order to achieve efficient delivery of polyamine effectors into the skin, studies were conducted using various formulations of liposomes (phospholipid-based vesicles, cationic liposomes, nonionic liposomes, non ionic/cationic liposomes, pegylated liposomes, PINC polymer, and propylene glycol and ethanol mixture (commonly used vehicle for administering minoxidil). First, these formulations were used to entrap reporter genes such as those encoding the marker proteins luciferase or beta-galactosidase, or a fluorescent probe (Nile Red), and their delivery was tracked in the target tissue by the functional assay of the marker proteins delivered or fluorescence emission in the case of Nile Red. The liposomes were prepared as set forth below.

Phospholipid based vesicles. The preparation contained the following lipid mixtures in a 1:0.5:0.1 molar ratio:
1. DSPC: Cholesterol: DOTAP
2. DOPE: Cholesterol: DSPC
3. DOPE-2000: Cholesterol: DSPC The lipids were dissolved in chloroform and evaporated in a rotoevaporater at 50° C. The dried lipid film was hydrated with HEPES buffer containing reporter DNA or one mg of Nile Red at RT for 30 min. The resulting suspension was subjected to five cycles of freezing and thawing. The final suspension was passed through 0.22 m filter seven times. The vesicles were stored at 4° C.

Nonionic liposomes. The nonionic liposome preparations contained glyceryl dilaurate (GDL), cholesterol, polyoxyethylene-10-stearyl ether (POE-10) at a weight percentage ratio of 58:15:27. The lipid mixture also contained 1% alpha-tocopherol. Appropriate amounts of the lipids were mixed (100 mg total lipid) and melted at 70° C. in a sterile polystyrene tube. The lipid mixture was drawn into a sterile syringe. A second syringe containing sterile PBS was preheated to 70° C. and connected via a 2-way stopcock to the lipid phase syringe. The aqueous phase was then slowly injected into the lipid phase syringe. The mixture was rapidly passed back and forth between the two syringes while being cooled under running cold tap water until the mixture reached room temperature. The final preparation was examined under a microscope to assure integrity and quality of the liposomes. Immediately before use, the liposome preparation was sonicated for 2 min at RT and an equal volume of reporter DNA (250 μg) was added and incubated at RT for an hour.

Nonionic/Cationic liposomes. The nonionic/cationic preparations contained GDL, POE—10, cholesterol, DOTAP (1,2 dioleyloxy-3(trimethylammonio) propane at a weight percent ratio of 50:23:15:12 in a 100 mg/ml preparation. Appropriate amounts of the lipids were mixed and melted in a polystyrene tube at 70° C. and drawn into a syringe preheated to 70° C. A second syringe containing sterile PBS was preheated to 70° C. and connected to the lipid phase syringe via a 2-way stopcock. The aqueous phase was slowly injected into the lipid phase syringe. The mixture was rapidly passed back and forth between the two syringes while being cooled under cold tap water until the mixture reached room temperature. Immediately before use, the liposomal suspension was sonicated for 2 min at RT and an equal volume of DNA (250 μg) and nonionic/cationic liposomes were mixed and incubated at RT for 1 hour.

PINC (Protective, Interactive and Non Condensing) polymers. Formulations were made by mixing 70% PVP, 30% Vinyl Acetate and 250 ug plasmid DNA in 0.9% NaCl and incubating at RT for 15 min.

PG (propylene glycol): Ethanol—plasmid DNA complex (Minoxidil vehicle). 250 μg of plasmid DNA was mixed with 60% PG, 20% Ethanol and 20% water and incubated at RT for 15 min before use.

To determine the efficiency of entrapment of the reporter genes, a DNA intercalation study with ethidium bromide was done to ensure that the DNA added has been entrapped in the liposomes. In brief, one ml of ethidium bromide (2 μg/ml) was added to an aliquot of the liposome preparation containing DNA and mixed for three seconds in a vortex mixer. As positive and negative controls, DNA and ethidium bromide and ethidium bromide alone were used. The ethidium bromide based fluorescence of all samples was monitored in a fluorimeter at an emission wavelength of 595 nm.

In vivo Experiments on Rat Pups. Animal experiments were conducted on six day old Harlan Sprague Dawley rat pups. 100 microliters of the liposome formulation containing the luciferase gene, or beta-galactosidase gene, or one mg Nile Red (Fluorescent probe) was applied at 30 min intervals onto a 1 square cm area of the back dorsal skin. Control pups received only the empty liposomes. After 24, 48 and 72 hours, the pups were sacrificed and the treated skin section was dissected out and used to analyze the expression of reporter genes or the level of fluorescent probe.

In situ beta-galactosidase assay. A portion of the skin section was embedded in OCT, sectioned and fixed as 5 um strips onto super frost slides with ice cold 1% formaldehyde, 0.2% glutaraldehyde, 2 mM $MgCl_2$ in PBS. The fixed tissues were washed at RT for 2 hours in three changes of PBS containing 2 mM $MgCl_2$, 0.1% sodium deoxycholate, 0.02% NP40. These were subsequently stained in the dark at 37° C. for 16 hours in 2 mg/ml 4-Cl-5-Br-3-indlyl-beta-galactopyranoside (X-Gal), 5 mM potassium ferricyanide, 5 mm potassium ferrocyanide, 2 mm $MgCl_2$, 0.02% NP40 and 0.1% sodiumdeoxy cholate in PBS. At the end of the incubation period, the slides were washed with PBS and counterstained in hemotoxylin and eosin for histological examination.

Preparation of tissue homogenate. The dissected skin section was cut into small pieces and homogenized in 2 ml of reporter lysis buffer (Promega) using a Polytron homogenizer. The homogenate was centrifuged at maximum speed for 15 min and the supernatant was used for further analyses. Protein content of the homogenate was determined using the BCA (Pierce) method.

Quantitative analysis of beta-galactosidase activity. Beta-galactosidase activity was measured by adding an aliquot of the tissue homogenate to an equal volume of 2× assay buffer (Promega), which contains the substrate (o-nitrophenyl beta-D-galactopyranoside). Samples were incubated for 30 min at 37° C. during which time the beta-galactosidase enzyme hydrolyzes the colorless substrate to 0-nitrophenol, which is yellow. The reaction was terminated by the addition of 1M of sodium carbonate and the absorbance was measured at 420 nm in a spectrophotometer. The activity was expressed as units/mg protein.

Quantitative analysis of luciferase activity. Luciferase activity was measured in the tissue homogenate using the Dual Luciferase assay Kit (Promega) following the manufacturer's instructions. In brief, to 100 microliter of the sample was added 100 microliters of the luciferase assay buffer containing the substrate and the light emitted immediately after the addition of Stop&Glo buffer was measured in a luminometer. The activity was expressed as RLU/mg protein.

Nile Red. Fluorescence emission of Nile Red was observed under a fluorescence microscope on skin sections.

Results:

Comparison of the efficiency of the delivery systems used. The efficiency of the liposomal delivery systems was compared in terms of the expressed product beta-galactosidase or luciferase in the treated skin section by measuring the activity of these two enzymes in the tissue homogenate per mg of the protein extracted. Rat pups treated with nonionic (NI) liposomes encapsulating 250 ug luciferase DNA showed maximum expression (95000 RLU/mg protein) after 24 hours of treatment versus NI+DOTAP, and PL formulations. Interestingly, PINC polymer, PEG and the minoxidil carrier system were found to be inefficient in the system described above. A similar trend was observed in the delivery of the beta-galactosidase gene and the fluorescent Nile Red. While this example is not intended to exclude the use of the other liposomal delivery systems, the nonionic liposome formulation was found to be a particularly efficient delivery system when compared to other delivery systems. These observations parallel the findings reported by Niemic et al (1997). They have reported that the perifollicular expression of human interleukin-1 receptor antagonist protein following topical application of liposome-plasmid DNA formulations was significantly higher with nonionic liposomes than phospholipid-based liposomes.

Example 5

Modification of Liposomes to Target the Gastrointestinal Mucosal Epithelium

In the setting of the gut, the incorporation of additional means to allow attachment of the liposomes to the epithelial cell surface would facilitate delivery of liposomal contents to these cells. To increase the specificity of liposomes for mucosal epithelial cells that line the stomach and upper small intestine, the cholera toxin B (CTB) subunit may be covalently attached to the surface of a liposome. Liposomes that have the CTB subunit attached to their surface attach with specificity to cells that express the M1 ganglioside receptor molecule on their surface. Cells that normally express this cell surface molecule include lumenal epithelial cells lining the stomach and upper small intestine. This is the means by which cholera bacterial cells attach to these cells in a natural infection. The B subunit of cholera toxin confers M1 ganglioside receptor binding, but in the absence of the A subunit, confers no toxicity.

Materials and Methods:

Liposome preparation for conjugation to cholera toxin B subunit Liposomes containing purified rat liver GSTs and trace FITC-conjugated rat liver GST were prepared and purified by the standard extrusion protocol, using the following mixture of lipids: phosphatidylcholine (PC): phosphatidylethnolamine (PE): 1,2-Dioleoyl-sn-glycero-3 phosphoethanolamine-N-[4]-(p-maleimidophenyl)butyrate (N-MBP-PE), 70:20:10 Mol %.

Chemical modification of cholera toxin B subunit (CTB) for cross-linking to liposomes. A primary amine reactive reagent was used to add thiol groups to the lysine residues of CTB. The thiol groups were necessary for reaction with the maleimide group on the N-MPB-PE-containing liposomes. To achieve this, CTB (100 μg) was dissolved in HEPES-saline buffer and incubated with N-succinimidyl 3-(2-pyridyldithio)propionate (SPDF) at a 1:100 molar ratio in the dark at room temperature for one hour. The reaction was quenched by adding 10 μl of 20 mM L-lysine in 20 mM Tris-HCl (pH 6.8) and the reaction products were then reduced by adding 5 μl of 7.7 mg/ml dithiothreitol in water. Unreacted substances were removed by passing the reaction mixture through a size exclusion Sephadex G25 spin column. The concentration of the activated CTB in the excluded fraction was measured by Coomassie protein assay reagent (Pierce Biochemical, Rockford, Ill.).

Cross-linking of activated CTB to liposomes. Conjugation of activated CTB to liposomes containing GST and trace FITC-conjugated GST was carried out by incubating the reduced CTB (50 g) with a suspension of 1 mL N-MBP-PE-bearing liposomes at 5° C. overnight. The coupling reaction was stopped by adding 10 μl of L-cysteine buffer (20 mM L-cysteine in 20 mM Tris-HCL buffer, pH7.2). The CTB-conjugated liposomes were purified from unconjugated CTB on a size exclusion gel filtration column (Biogel A-15 m gel, Bio-Rad Laboratories, Calif.; 15 cm long×2 cm diameter) pre-equilibrated with HEPES-saline buffer. The liposomes were eluted in 0.5 ml fractions and the liposome content of each fraction was determined by fluorescence and GST activity. Liposome-containing fractions were pooled (fractions #5–9) and concentrated to 1 ml by centrifugation at 1000×g for 30 min using a Centriprep 500 concentrator (Amicon Inc., Beverly Mass.).

Cellular uptake of CTB liposomes. Cells (6×106 HuTu or COS cells) were seeded into 60 mm dishes and grown overnight in DMEM with high glucose (DMEM w/HG) supplemented with 10% fetal calf serum (FCS) in a humidified atmosphere of 10% CO2. The monolayers were then washed three times with 5 ml of DMEM w/HG+HEPES saline (50 mM HEPES+50 mM NaCl, ph 7.5). To test the ability of the CTB-conjugated liposomes to bind specifically to cells bearing the GM1 ganglioside receptor, some dishes were pretreated for 10 min with a commercially-available sample of GM1 ganglioside receptor (20 μg). A 100 μl sample of CTB-conjugated liposomes (containing 5000 fluorescence units of FITC-conjugated GST) was added to each monolayer with 5 ml DMEM w/HG+HEPES saline buffer, and incubated for 4 hours at 37 C. The cell monolayers were then washed 4 times with 5 ml PBS to remove unbound CTB-conjugated liposomes. The amount of CTB-conjugated liposomes bound/internalized to the cells was quantified by first scraping the cells from the culture dish, resuspending in 0.3 ml PBS and sonicating for 30 seconds. A 20 μl aliquot of each cell lysate was added to 2 ml of PBS, and the amount of cell-associated fluorescence was measured (excitation/emission maxima 494/520 nm) in a fluorometer. The concentration of protein in the cell lysate was determined using the Coomassie protein estimation kit.

Results:

The use of liposomes having the CTB subunit attached to the liposome surface resulted in enhanced delivery of labeled protein to gastrointestinal carcinoma cells (HuTu cells), but not to kidney tubule epithelial cells (COS cells). The increased efficiency conferred by the CTB subunit was quenched in the presence of an excess of free M1 Ganglioside receptor. These results demonstrate that liposomes are effectively modified to target cells of the gastrointestinal epithelium by incorporation of the CTB subunit onto their surfaces.

Example 6

Prevention of Chemotherapy-Induced Alopecia by Topical Application of Non-Natural Polyamine Analogs Results set forth in this example demonstrate that topically administered polyamine analogs are effective against chemotherapy-induced alopecia in a rat model of chemotherapy-induced alopecia. This animal model mimics many of the features found in chemotherapy-induced alopecia seen in humans and is considered a clinically-relevant model for testing novel therapeutics.

Materials and Methods:

Induction of alopecia by cytoxan (CTX). Lactating Sprague Dawley mother rats with rat pups were purchased from Harlan Sprague Dawley (Indianapolis, Ind.). The mother rats were given food and water ad libitum. The rats pups were tested in the model of chemotherapy-induced alopecia described by Hussein A. M. et al., Science: 249, 1564 (1990). Cytoxan (CTX), a chemotherapeutic widely used in the treatment of cancer, was used to induce alopecia in the rats. A common side effect of cytoxan in patients is alopecia. Cytoxan and polyamine effector compounds were purchased from Sigma Chemicals Co. (St. Louis, Mo.). To produce CTX-induced alopecia, 7 to 10 day old rat pups were injected i.p. with 35 mg/kg of CTX prepared in phosphate-buffered saline. To produce reproducible CTX induced alopecia, we first tested several concentrations (35, 40, 45 ug/gm body weight) of CTX in phosphate-buffered saline (PBS), which was injected i.p. in 7–10 day old pups. Seven to ten days after CTX treatment the pups were examined to determine the degree of hair loss. The density of hair on the pups was then determined. 100% hair density represents that found on the untreated control pups while 0% represented pups with total hair loss. It was observed that 35 μg/gm of CTX was sufficient to induce 100% hair loss approximately 7 days after cytoxan challenge, and this concentration was used in subsequent experiments.

Different classes of non-natural polyamine analogs were tested in this model. The effector analogs were prepared in a delivery vehicle, consisting of 70% ethanol in water. The compounds in ethanol/water solution, from 50–150 μl in volume, were topically administered to the backs of the pups once per day before and after CTX challenge. Using a micropipette, the formulation was applied to approximately 2 cm$^2$ section of skin to the backs of the rat pups. Specifically, the pups were treated once daily for the 4–5 days before CTX challenge, one the day of CTX challenge and 5 days afterwards. Control groups consisted of pups receiving only delivery vehicle. Control groups treated with delivery vehicle were tested as part of every treatment study. Two to seven animals were tested per group in both the control and test groups.

Approximately 7 to 10 days after CTX treatment, the pups were evaluated for the presence of alopecia. Hair loss was evaluated using a modified alopecia-scoring index described by Chen G. et al., Int. J. Cancer: 75, 303 (1998). A score of 0=no hair loss; a score of 1=10–30% hair loss; a score of 2=40–60% hair loss; a score of 3=70–90% hair loss; and a score of 4=100% hair loss.

Polyamine analogs tested. Different classes of polyamine analogs were obtained from SLIL Biomedical Corporation (Madison, Wis.). Nineteen different analogs were tested in the alopecia model. The classes fall under three categories: first generation simple analogs of natural polyamines, second generation conformationally restricted analogs of polyamines (e.g. SL-11093, SL-11047, SL-11099 and third generation oligoamines or linked polyamine analogs (e.g. SL-11159, SL-11158, SL-11172, SL-11144, SL-11160). The compounds were tested at 5 mM.

Results:

Results indicate that several analogs were effective at preventing alopecia caused by CTX. The results using the different treatments and their molecular weights are shown in Table 8. Using the concentration and dosing conditions specified, polyamine analogs, SL-11237, SL-11159, SL-11047, SL-11144, SL-11158, SL-11160, SL-11227, SL-11179, SL-11101, SL-11092, and SL-11094 effectively prevented alopecia in this model, producing alopecia scores of 2.0 or less. Rats pups treated with these compounds retained about 50–90% of their hair. In contrast, pups treated with vehicle consistently lost 100% of their hair. A second set of compounds (SL-11093, SL-11241, SL-11122, SL-11172, and SL-11103) was moderately effective with average alopecia scores of less than 3.0. Under the treatment conditions, several other compounds such as SL-11244, SL-11246, SL-11179, and SL-11141 were less effective at preventing alopecia after CTX treatment.

TABLE 8

| Structure Source | Treatment (mw) | Avg Alopecia Score* |
|---|---|---|
|  | Vehicle** | 4.0 |
| B, D | SL-11093 † (444) | 2.3 |
| D | SL-11159 ‡ (1078) | 1.8 |
| A, D | SL-11047 † (402) | 1.0 |
| B, D | SL-11099 † (458) | 3.0 |
| C, D | SL-11144 ‡ (1075) | 2.0 |
| D | SL-11158 ‡ (860) | 1.5 |
| D | SL-11160 (862) | 2.0 |
| D | SL-11094 (452) | 1.5 |
| C, D | SL-11122 (537) | 2.5 |
| B, C, D | SL-11103 (428) | 2.5 |
| C, D | SL-11141 (555) | 3.3 |
| B, D | SL-11102 (430) | 3.5 |
| C, D | SL-11091 (400) | 3.0 |
| A, D | SL-11038 (416) | 3.5 |
| D | SL-11050 (248) | 3.5 |
| B, C, D | SL-11101 (430) | 1.0 |
| A, D | SL-11044 (430) | 2.5 |
| C, D | SL-11092 (372) | 0.0 |

† constrained polyamine
‡ oligoamine/linked polyamine
*Hair loss was determined using an alopecia scoring scheme (Chen G., et al.): 0 = no hair loss, 1 = 10–30% hair loss, 2 = 40–60% hair loss, 3 = 70–90% hair loss, and 4 = 100% hair loss.
**This control was re-run in every independent experiment Source of Published Structure:
A: U.S. Pat. No. 5,889,061
B: J. Med. Chem. 44:390, 2001
C: WO 00/66587A2
D: WO02/38105A2

Example 7

Prevention of Radiation-Induced Dermatitis by Topical Application of Polyamine Analog SL-11159

Materials and Methods:

To determine if treatment with a non-natural polyamine analog could effectively prevent radiation-induced dermatitis, adult rats were topically treated with a polyamine analog before and after radiation treatment. Rats were exposed to medically relevant levels of radiation that could induce clinical radiation dermatitis. Sprague Dawley rats (Harlan Spraque Dawley) at 4–6 weeks old were anesthetized with sodium pentobarbital at 40 mg/kg body weight (Sigma, St. Louis, Mo.) prior to radiation exposure. A defined, depilated area on the backs of rats was irradiated using a Mark I, Model 30, Cs 137 irradiator (J. L. Sheppard & Associates). Briefly, back hair was removed to expose the skin by using Oster electric clippers followed by a safety razor. The rest of the body was protected from radiation exposure using a lead shield. A dose response study was initially preformed to reproduce relevant dermatitis that matched the Grade (I–IV) scale used to score the severity of radiation-induced dermatitis in the clinical setting. Radiation doses of 5–7 Gray (1 Gray (Gy)=100 mrem) produced Grade I dermatitis within 8–10 days. Radiation doses of 7–10 Gy produced Grade II dermatitis within 8–10 days. After 8–10 days, severe radiation dermatitis was produced at 20–25 Gy (Grade III dermatitis) or at 30–35 Gy (Grade IV). Radiation dermatitis of Grade II–III was considered most clinically relevant, so a radiation challenge dose of 15 Gy in the rats was used in subsequent treatment experiments.

The polyamine analog SL-11159 was selected for testing in this experiment because it was found to be effective in preventing CTX-induced alopecia (Example 1). The analog at 10 mM was prepared in a delivery vehicle consisting of phosphate-buffered saline containing 3% hydroxypropylmethyl-cellulose (HPC). HPC was added to form an aqueous gel delivery vehicle to improve topical residence time. The compound at 100 μl in volume was topically administered to the shaved region on the rats. This region was treated topically with 10 mM polyamine analog once daily for 5 days before and 5 days after radiation challenge. Rats treated with only the gel delivery vehicle served as controls. Two to three rats were tested per treatment group. Eight to ten days post-radiation challenge, the rats were evaluated for dermatitis using a modified scoring scale described by Masuda K. et al. Int. J. Radiation Oncol. Biol. Phys: 12, 1645 (1986). Dermatitis score of 0=normal, 1=slight redness, scaly skin with no focal lesions, 2=moderate redness, breakdown of larger area, some small focal lesions, 3=skin very red, large or many focal ulcers and crusty lesions, 4=skin very red, breakdown of the entire irradiated area, severe exudation and large crusty lesions.

Results

Polyamine analog SL-11159 was found to be effective at preventing radiation-induced dermatitis in the rat. Results are shown in Table 9. Dermatitis scores of about 2–3, or roughly equivalent to Grade III dermatitis were seen in the rats treated with only delivery vehicle. In contrast, topical treatment with SL-11159 effectively reduced the severity of the dermatitis, producing an average dermatitis score of 1.0. These results indicate that treatments with topical polyamine analogs can effectively reduce radiation-induced dermatitis.

TABLE 9

| Treatment | Avg dermatitis score* |
|---|---|
| Gel vehicle | 2.3 |
| SL-11159 | 1.0 |

*0 = normal, 1 = slight redness, scaly skin with no focal lesions, 2 = moderate redness, breakdown of larger area, some small focal lesions, 3 = skin very red, breakdown of most of the irradiated area, large ulcers and crusty lesions, 4 = skin very red, breakdown of the entire irradiated area, severe exudation and large crusty lesions.

Example 8

Prevention of Chemotherapy- and Radiotherapy-Induced Alopecia and Dermatitis by Topical Application of Different Classes of Polyamines Alopecia was induced in rat pups by Cytoxan, cytarbine, doxorubicin and radiation, according to the methods described in the previous examples. Polyamines from three different structural families, obtained from two different sources, gave excellent results in animal alopecia models for Cytoxan, cytarbine and doxorubicin.

Results are shown in Tables 10–15 below.

TABLE 10

Summary of Alopecia Scores for the Cytoxan-Induced Alopecia Model in Rat Pups treated with selected polyamine analogs

| Treatment* (1 mM) | Alopecia Scores** | Avg Alopecia Score | Polyamine Structure Family | Source |
|---|---|---|---|---|
| SL-11047 | 1, 1 | 1.0 | Conformationally Restricted | SLIL |
| SL-11092 | 0, 0 | 0.0 | Conformationally Restricted | SLIL |
| SL-11094 | 1, 2, 1, 2 | 1.5 | Conformationally Restricted | SLIL |
| SL-11159 | 1, 2, 1, 1, 1, 2, 3, 4, 0, 2, 1, 0, 0, 1, 1 | 1.3 | Oligoamine | SLIL |
| SL-11160 | 2, 4, 0, 1, 1, 1 | 1.5 | Oligoamine | SLIL |

*Vehicle control alopecia score = 4.0
**Hair loss was determine using an alopecia scoring scheme (Chen G., et al.): 0 = no hair loss, 1 = 10–30% hair loss, 2 = 40–60% hair loss, 3 = 70–90% hair loss, and 4 = 100% hair loss

TABLE 11

Summary of Alopecia Scores for the Cytoxan-Induced Alopecia Model in Rat Pups treated with polyamines from different structural families
Alopecia Score* +/− SEM

| Treatment | | | Expt. 1 | Expt. 2 | Expt. 3 |
|---|---|---|---|---|---|
| Vehicle | Polyamine Structure Family | Source | 4.0 +/− 0.0 | 3.5 +/− 0.7 | 4.0 +/− 0.0 |
| BE-3-3-3 (10 mM) | Linear | Geltex | 1.5 +/− 0.7 | 0.25 +/− 0.3 | 2.0 +/− 0.3 |
| BE-3-3-3 (1 mM) | Linear | Geltex | 3.5 +/− 0.7 | 2.5 +/− 0.3 | 2.7 +/− 0.4 |

*Hair loss was determined using an alopecia scoring scheme (Chen G., et al.): 0 = no hair loss, 1 = 20–30% hair loss, 2 = 40–60% hair loss, 3 = 70–90% hair loss, 4 = 100% hair loss. Combined data of BE-3-3-3 at 10 mM was significant (P < 0.01) using Mann-Whitney U test.

TABLE 12

Summary of Alopecia Scores for the Cytarbine-Induced Alopecia Model in Rat Pups

| Treatment* (1 mM) | Expt # | Alopecia Scores** | Avg Alopecia Scores |
|---|---|---|---|
| SL-11093 | 114, 123 | 4, 3, 2, 3 | 3.0 |
| SL-11094 | 114 | 3, 0 | 1.5 |
| SL-11144 | 123 | 2, 4 | 3.0 |
| SL-11159 | 114, 123 | 0, 0, 1, 1 | 0.5 |
| SL-11160 | 114, 123 | 1, 3, 1, 1 | 1.5 |

*Vehicle control alopecia score - 4.0
**Hair loss was determined using an alopecia scoring scheme (Chen G., et al.): 0 = no hair loss, 1 = 10–30% hair loss, 2 = 40–60% hair loss, 3 = 70–90% hair loss, and 4 = 100% hair loss

TABLE 13

Summary of Alopecia Scores for the Doxorubicin-Induced Alopecia Model in Rat Pups

| Treatment* | Alopecia Scores** | Avg Alopecia Score |
|---|---|---|
| SL-11093 | 1, 1, 1, 1, 0, 0 | 0.7 |
| SL-11094 | 1, 4, 2, 0, 4, 1 | 2.0 |
| SL-11144 | 0, 0 | 0.0 |
| SL-11160 | 2, 4, 0, 0, 0 | 1.2 |

*Vehicle control Alopecia score - 4.0
**Hair loss was determined using an alopecia scoring scheme (Chen G., et al.): 0 = no hair loss, 1 = 10–30% hair loss, 2 = 40–60% hair loss, 3 = 70–90% hair loss, and 4 = 100% hair loss

TABLE 14

Summary of Radiation Dermatitis Scores in the Rat Model Challenged with 15 Gy Radiation

| Treatment* | Expt # | Dermatitis Scores | Avg Dermatitis Score |
|---|---|---|---|
| Vehicle | 95, 112, 121 | 3, 3, 1, 3, 3, 2, 2, 2, 3, 3 | 2.5 |
| SL-11159 (1 mM) | 112, 121 | 2, 1, 1, 2, 1 | 1.4 |
| SL-11159 (10 mM) | 95, 112 | 2, 1, 1, 1, 1, 1 | 1.2 |
| SL-11160 (1 mM) | 121 | 2, 1, 2 | 1.6 |

*gel or PG vehicle
**Radiation-induced dermatitis was determined using a modified scoring scheme from Masuda K., et al.: 0 = normal, 1 = slight redness with scaling of skin, 2 = moderate redness, low numbers of small focal lesions, 3 = skin red, breakdown of some of the irradiated area, high numbers of focal lesions, and/or large crusty focal lesions, and 4 = skin very red, breakdown of entire irradiated area, severe exudation and large crusty lesion covering entire irradiated area.

Set forth below is a table showing alopecia scores in the rat model for particularly effective polyamine effectors as demonstrated in the previous examples. A representative result is also shown in FIG. 1.

Following the initial screening process, compounds for re-screening were selected on the basis of their ability to produce alopecia scores of 2 or less (hair retention of 40% or more). The alopecia scoring system is shown at the bottom of the table. The compounds shown in the table below were found to be significantly more effective in alopecia reduction/prevention than most of the other compounds that were tested. Specifically, results for six very effective compounds that prevent hair loss (>70% hair retention) in about 90% of the treated animals are shown.

For comparison, in related work, Davis et al. (Science 291:134, 2001) scored any animal with retention of 50% of its hair as "positive," and in their Cytoxan experiments, they scored 30% of the animals as "positives." Moreover, Davis et al. indicate that "greater than 50% hair loss on a human scalp is required for a clearly noticeable cosmetic change." According to that criterion, 90% of the animals treated with the compounds shown in Table 15 have cosmetically normal hair density.

TABLE 15

Summary of Alopecia Scores for Cytoxan-Induced Alopecia Model in Rat Pups

| Treatment | Alopecia Scores* | Avg Alopecia Score |
|---|---|---|
| SL-11047 | 1, 1 | 1.0 |
| SL-11092 | 0, 0 | 0.0 |
| SL-11094 | 1, 2, 1, 2 | 1.5 |
| SL-11159 | 1, 2, 1, 1, 1, 2, 0, 4, 2, 1 | 1.5 |

TABLE 15-continued

Summary of Alopecia Scores for Cytoxan-Induced
Alopecia Model in Rat Pups

| Treatment | Alopecia Scores* | Avg Alopecia Score |
|---|---|---|
| SL-11160 | 2, 4, 0, 1, 1, 1 | 1.5 |
| BE-3-3-3 | Several data sets at multiple concentrations of BE-3-3-3 | 0.3–1.5 |

*Hair loss was determined using an alopecia scoring scheme (Chen G., et al.): 0 = no hair loss, 1 = 10–30% hair loss, 2 = 40–60% hair loss, 3 = 70–90% hair loss, and 4 = 100% hair loss The present invention is not limited to the embodiments described and exemplified above, but is capable of variation and modification without departure from the scope of the appended claims.

We claim:

1. A method for reducing or inhibiting chemotherapy- or radiotherapy-induced alopecia in a patient undergoing treatment with a chemotherapeutic agent or radiation therapy, which comprises administering to the patient's scalp a pharmaceutical preparation comprising at least one polyamine effector selected from the group consisting of spermine, putrescine, norspermidine, cadaverine, spermidine, agmatine, NG-hydroxy-arginine, DL-alpha-difluoromethylorinithine, BE-3-3-3, SL-11237, SL-11159, SL-11047, SL-11144, SL-11158, SL-11160, SL-11227, SL-11179, SL-11101, SL-11092, SL-11094, SL-11093, SL-11341, SL-11122, SL-11172, SL-11103, SL-11244, SL-11246, and SL-11179, and a topical delivery vehicle for locally delivering the polyamine effector to cells lining hair follicles, in an amount and for a time effective to reduce or inhibit the chemotherapy- or radiotherapy-induced alopecia in the patient.

2. The method of claim 1, wherein the pharmaceutical preparation is administered beginning at least one day prior to chemotherapy or radiation therapy.

3. The method of claim 2, wherein the pharmaceutical preparation is administered beginning at least five days prior to chemotherapy or radiation therapy.

4. The method of claim 1, wherein the pharmaceutical preparation is administered after initiation of chemotherapy or radiation therapy.

5. The method of claim 1, wherein the pharmaceutical preparation is administered throughout a course of chemotherapy or radiation therapy.

6. The method of claim 1, wherein the pharmaceutical preparation is administered following termination of a course of chemotherapy or radiation therapy.

7. The method of claim 1, wherein the topical delivery vehicle comprises one or more of liposomes, lipid droplet emulsions, oils, aqueous emulsions of polyoxyethylene ethers, aqueous alcohol mixtures, aqueous ethanol mixtures containing propylene glycol, aqueous ethanol mixtures containing phosphatidyl choline, lysophosphatidyl choline and triglycerides, xanthan gum in aqueous buffer, hydroxypropymethylcellulose in aqueous buffer or aqueous alcohol mixtures, diethylene glycol monoethyl ether in aqueous buffer, and biodegradable microparticles.

8. The method of claim 7, wherein the topical delivery vehicle comprises an aqueous alcohol mixture.

9. The method of claim 8, wherein the topical delivery vehicle further comprises propylene glycol.

10. The method of claim 1, wherein the pharmaceutical preparation is formulated as a cream, lotion, ointment or gel.

* * * * *